US012331342B2

(12) United States Patent
Scrutton et al.

(10) Patent No.: US 12,331,342 B2
(45) Date of Patent: Jun. 17, 2025

(54) LINALOOL SYNTHASES

(71) Applicant: C3 BIOTECHNOLOGIES LIMITED, Lancaster (GB)

(72) Inventors: Nigel Scrutton, Manchester (GB); Nicole Leferink, Manchester (GB)

(73) Assignee: C3 BIOTECHNOLOGIES LIMITED, Lancaster (GB)

( * ) Notice: Subject to any disclaimer, the term of this patent is extended or adjusted under 35 U.S.C. 154(b) by 723 days.

(21) Appl. No.: 17/595,643

(22) PCT Filed: May 19, 2020

(86) PCT No.: PCT/EP2020/063988
§ 371 (c)(1),
(2) Date: Nov. 19, 2021

(87) PCT Pub. No.: WO2020/234307
PCT Pub. Date: Nov. 26, 2020

(65) Prior Publication Data
US 2022/0213510 A1 Jul. 7, 2022

(30) Foreign Application Priority Data

May 20, 2019 (GB) ..................................... 1907088

(51) Int. Cl.
*C12N 9/88* (2006.01)
*C12N 15/74* (2006.01)
*C12P 5/00* (2006.01)

(52) U.S. Cl.
CPC ................ *C12P 5/007* (2013.01); *C12N 9/88* (2013.01); *C12N 15/74* (2013.01); *C12Y 402/03025* (2013.01); *C12Y 402/03026* (2013.01)

(58) Field of Classification Search
None
See application file for complete search history.

(56) References Cited

U.S. PATENT DOCUMENTS

2018/0291402 A1 10/2018 Hoshino et al.
2018/0291403 A1 10/2018 Hoshino et al.

FOREIGN PATENT DOCUMENTS

| CN | 107937431 A | 4/2018 |
|---|---|---|
| JP | 2013013406 A | 1/2013 |
| JP | 2017169448 A | 9/2017 |
| WO | 2013016591 A1 | 1/2013 |
| WO | 2013071172 A1 | 5/2013 |
| WO | 2017100655 A1 | 6/2017 |
| WO | 2018142109 A1 | 8/2018 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Franceus et al., J. Ind. Microbiol. Biotechnol. vol. 44, pp. 687-695, 2017.*
Cao et al. Bioresource technology, vol. 245, No. Pt B, pp. 1641-1644, Dec. 2017.*
CN Office Action for Application No. 202080049581.1, dated Jun. 29, 2023, 7 pages.
PCT International Search Report and Written Opinion for International Application No. PCT/EP2020/063988, dated Jun. 30, 2020, 17 pages.
Leferink et al., "Experiment and Simulation Reveal How Mutations in Functional Plasticity Regions Guide Plant Monoterpene Synthase Product Outcome," ACS Catalysis, 2018, 8, 3780-3791.
Karuppiah et al., "Structural Basis of Catalysis in the Bacterial Monoterpene Synthases Linalool Synthase and 1,8-Cineole Synthase," ACS Catalysis, 2017, 7, 6268-6282.
Nakano et al., "Identification and Characterization of the Linalool/ Nerolidol Synthase from Streptomyctes Clavuligerus," Chembiochem, vol. 12, No. 16, Nov. 4, 2011, 5 pages.
Aharoni et al., "Volatile science? Metabolic engineering of terpernoids in plants," Trends in Plant Science, vol. 10, No. 12, Dec. 2005, 9 pages.
Cseke et al., "Structure and Evolution of Linalool Synthase," Mol. Biol. Evol., 15(11), 1998, 1491-1498.
Hu et al., "Genome Mining in *Streptomyces clavuligerus*: Expression and Biochemical Characterization of Two New Cryptic Sesquiterpene Synthases," Chemistry & Biology, 18, 32-37, Jan. 28, 2011.

* cited by examiner

*Primary Examiner* — Richard G Hutson
(74) *Attorney, Agent, or Firm* — Hoffman Warnick LLC

(57) ABSTRACT

Linalool synthase variants are disclosed. The variants preferably comprise an amino acid sequence having one or more amino acid substitutions. Variants producing a greater linalool yield and/or higher linalool:nerolidol ratio compared with the corresponding wild type linalool synthase are also disclosed. A method comprising the conversion of geranyl pyrophosphate to linalool using a linalool synthase variant is also disclosed.

21 Claims, 12 Drawing Sheets
Specification includes a Sequence Listing.

| Mutation | Primer name | Sequence (5' → 3') |
| --- | --- | --- |
| L72F | bLinS-L72F_fw | CTGTGTGTTGATGTTtTcGGTTGGACCTTTCTG (SEQ ID NO: 14) |
| L72M | bLinS-L72M_fw | CTGTGTGTTGATGTTaTGGGTTGGACCTTTCTG (SEQ ID NO: 15) |
| L72I | bLinS-L72I_fw | CTGTGTGTTGATGTTaTtGGTTGGACCTTTCTG (SEQ ID NO: 16) |
| L72N | bLinS-L72N_fw | CTGTGTGTTGATGTTaccGGTTGGACCTTTCTG (SEQ ID NO: 17) |
| L72Q | bLinS-L72Q_fw | CTGTGTGTTGATGTTCaGGGTTGGACCTTTCTG (SEQ ID NO: 18) |
| T75F | bLinS-T75F_fw | GATGTTCTGGGTTGGttCTTTCTGTTTGATGATC (SEQ ID NO: 19) |
| T75M | bLinS-T75M_fw | GATGTTCTGGGTTGGAtgTTTCTGTTTGATGATC (SEQ ID NO: 20) |
| I176F | bLinS-I176F_fw | GCTCGCCATCGTACCtTTTGTTGTCGTCCGC (SEQ ID NO: 21) |
| C177F | bLinS-C177F_fw | CATCGTACCATTTGTTtttCGTCCGCTGTTTG (SEQ ID NO: 22) |
| C178F | bLinS-C178F_fw | CATCGTACCATTTGTTtTCGTCCGCTGTTTG (SEQ ID NO: 23) |
| C178M | bLinS-C178M_fw | CATCGTACCATTTGTatgCGTCCGCTGTTTG (SEQ ID NO: 24) |
| V214F | bLinS-V214F_fw | CCACCAGTGATGCAtTTATTGGTATGAATG (SEQ ID NO: 25) |
| V214L | bLinS-V214L_fw | CCACCAGTGATGCAcTgATTGGTATGAATG (SEQ ID NO: 26) |
| V214I | bLinS-V214I_fw | CCACCAGTGATGCAaTTATTGGTATGAATG (SEQ ID NO: 27) |
| V214M | bLinS-V214M_fw | CCACCAGTGATGCAaTgATTGGTATGAATG (SEQ ID NO: 28) |
| V214S | bLinS-V214S_fw | CCACCAGTGATGCAagTATTGGTATGAATG (SEQ ID NO: 29) |
| F295W | bLinS-F295W_fw | GCACTGAGCGCATggTGTCGTGGTTATC (SEQ ID NO: 30) |
| F295Y | bLinS-F295Y_fw | GCACTGAGCGCATaTTGTCGTGGTTATC (SEQ ID NO: 31) |

Figure 6

| Plasmid reference | Plasmid name | Description - Origin of replication, Antibiotic marker, Promoters and Operons | Source |
|---|---|---|---|
| pMVA | BbA5a-MTSAe-T1f-MBI(f)-T1002i | p15A, Kanr, PlacUV5, MTSA, T1, MBI-f, T1002 | Leferink et al. 2016 |
| pGPPSmTC/S38 | pBbB2a-trAgGPPS(co)-blinS | pBBR, Ampr, Ptet, trAgGPPS(co)-blinS | Karuppiah et al. 2017 |
| pGPPSmTC/S38-L72F | pBbB2a-trAgGPPS(co)-blinS-L72F | pBBR, Ampr, Ptet, trAgGPPS(co)-blinS-L72F | This study |
| pGPPSmTC/S38-L72I | pBbB2a-trAgGPPS(co)-blinS-L72I | pBBR, Ampr, Ptet, trAgGPPS(co)-blinS-L72I | This study |
| pGPPSmTC/S38-L72N | pBbB2a-trAgGPPS(co)-blinS-L72N | pBBR, Ampr, Ptet, trAgGPPS(co)-blinS-L72N | This study |
| pGPPSmTC/S38-L72Q | pBbB2a-trAgGPPS(co)-blinS-L72Q | pBBR, Ampr, Ptet, trAgGPPS(co)-blinS-L72Q | This study |
| pGPPSmTC/S38-T75F | pBbB2a-trAgGPPS(co)-blinS-T75F | pBBR, Ampr, Ptet, trAgGPPS(co)-blinS-T75F | This study |
| pGPPSmTC/S38-C178F | pBbB2a-trAgGPPS(co)-blinS-C178F | pBBR, Ampr, Ptet, trAgGPPS(co)-blinS-C178F | This study |
| pGPPSmTC/S38-I176F | pBbB2a-trAgGPPS(co)-blinS-I176F | pBBR, Ampr, Ptet, trAgGPPS(co)-blinS-I176F | This study |
| pGPPSmTC/S38-C177F | pBbB2a-trAgGPPS(co)-blinS-C177F | pBBR, Ampr, Ptet, trAgGPPS(co)-blinS-C177F | This study |
| pGPPSmTC/S38-V214F | pBbB2a-trAgGPPS(co)-blinS-V214F | pBBR, Ampr, Ptet, trAgGPPS(co)-blinS-V214F | This study |
| pGPPSmTC/S38-F295W | pBbB2a-trAgGPPS(co)-blinS-F295W | pBBR, Ampr, Ptet, trAgGPPS(co)-blinS-F295W | This study |
| pGPPSmTC/S38-L72M | pBbB2a-trAgGPPS(co)-blinS-L72M | pBBR, Ampr, Ptet, trAgGPPS(co)-blinS-L72M | This study |
| pGPPSmTC/S38-T75M | pBbB2a-trAgGPPS(co)-blinS-T75M | pBBR, Ampr, Ptet, trAgGPPS(co)-blinS-T75M | This study |
| pGPPSmTC/S38-C178M | pBbB2a-trAgGPPS(co)-blinS-C178M | pBBR, Ampr, Ptet, trAgGPPS(co)-blinS-C178M | This study |
| pGPPSmTC/S38-V214L | pBbB2a-trAgGPPS(co)-blinS-V214L | pBBR, Ampr, Ptet, trAgGPPS(co)-blinS-V214L | This study |
| pGPPSmTC/S38-V214I | pBbB2a-trAgGPPS(co)-blinS-V214I | pBBR, Ampr, Ptet, trAgGPPS(co)-blinS-V214I | This study |
| pGPPSmTC/S38-V214M | pBbB2a-trAgGPPS(co)-blinS-V214M | pBBR, Ampr, Ptet, trAgGPPS(co)-blinS-V214M | This study |
| pGPPSmTC/S38-V214S | pBbB2a-trAgGPPS(co)-blinS-V214S | pBBR, Ampr, Ptet, trAgGPPS(co)-blinS-V214S | This study |
| pGPPSmTC/S38-F295Y | pBbB2a-trAgGPPS(co)-blinS-F295Y | pBBR, Ampr, Ptet, trAgGPPS(co)-blinS-F295Y | This study |
| pGPPSmTC/S38-F295W | pBbB2a-trAgGPPS(co)-blinS-F295W | pBBR, Ampr, Ptet, trAgGPPS(co)-blinS-F295W | This study |
| pGPPSmTC/S38-L72F-C177F | pBbB2a-trAgGPPS(co)-blinS-L72F-C177F | pBBR, Ampr, Ptet, trAgGPPS(co)-blinS-L72F-C177F | This study |
| pGPPSmTC/S38-T75F-C177F | pBbB2a-trAgGPPS(co)-blinS-T75F-C177F | pBBR, Ampr, Ptet, trAgGPPS(co)-blinS-T75F-C177F | This study |
| pGPPSmTC/S38-L72F-T75-C177F | pBbB2a-trAgGPPS(co)-blinS-L72F-T75-C177F | pBBR, Ampr, Ptet, trAgGPPS(co)-blinS-L72F-T75-C177F | This study |

Figure 7

| Variant | Linalool | Nerolidol | Geranoids | Farnesol[a] | Reference |
|---|---|---|---|---|---|
| WT bLinS | 363.3 ± 57.9 | 159.1 ± 7.3 | 36.7 ± 0.8 | 31.5 ± 3.7 | Karuppiah et al. 2017 |
| bLinS-L72F | 2.7 ± 1.6 | ND | 24.3 ± 11.1 | 8.3 ± 9.4 | This study |
| bLinS-L72M | 429.1 ± 12.1 | 43.8 ± 1.9 | 26.5 ± 4.0 | 6.2 ± 1.6 | This study |
| bLinS-L72I | 1.1 ± 0.2 | ND | 13.9 ± 6.3 | 1.7 ± 2.0 | This study |
| bLinS-L72N | 0.03 ± 0.05 | ND | 20.9 ± 12.3 | 5.7 ± 2.8 | This study |
| bLinS-L72Q | 0.2 ± 0.1 | ND | 19.1 ± 7.1 | 1.7 ± 0.2 | This study |
| bLinS-T75F | ND | ND | 40.8 ± 14.1 | 15.5 ± 11.1 | This study |
| bLinS-T75M | 1.7 ± 1.2 | 0.1 ± 0.2 | 31.4 ± 13.6 | 2.3 ± 2.3 | This study |
| bLinS-I176F | ND | ND | 17.5 ± 13.3 | | This study |
| bLinS-C177F | ND | ND | 28.0 ± 13.0 | 9.2 ± 2.4 | This study |
| bLinS-C178F | ND | ND | 19.5 ± 17.6 | | This study |
| bLinS-C178M | 4.8 ± 0.1 | 0.5 ± 0.0 | 55.9 ± 11.1 | 1.4 ± 0.2 | This study |
| bLinS-V214F | ND | ND | 7.7 ± 11.4 | | This study |
| bLinS-V214L | 49.2 ± 4.8 | 2.1 ± 0.8 | 79.1 ± 8.2 | 2.0 ± 0.4 | This study |
| bLinS-V214I | 265.3 ± 39.2 | 109.7 ± 52.1 | 6.8 ± 1.5 | 9.3 ± 10.8 | This study |
| bLinS-V214M | 0.9 ± 0.7 | ND | 6.1 ± 6.7 | 1.7 ± 1.8 | This study |
| bLinS-V214S | 0.2 ± 0.1 | ND | 21.8 ± 9.1 | 1.8 ± 0.9 | This study |
| bLinS-F295W | 0.2 ± 0.4 | ND | 34.9 ± 9.8 | 6.6 ± 5.6 | This study |
| bLinS-F295Y | 1.4 ± 0.5 | 0.6 ± 0.3 | 51.4 ± 16.5 | 1.5 ± 1.1 | This study |
| bLinS-L72F-C177F | ND | ND | 14.1 ± 12.2 | 15.7 ± 8.9 | This study |
| bLinS-T75F-C177F | ND | ND | 72.6 ± 33.2 | 31.9 ± 21.4 | This study |
| bLinS-L72F-T75F-C177F | ND | ND | 63.6 ± 12.6 | 18.9 ± 1.9 | This study |

Figure 12

| Variant | Linalool | Nerolidol | Geranoids | Farnesol | Linalool:nerolidol ratio |
|---|---|---|---|---|---|
| WT bLinS | 363.3 ± 57.9 | 159.1 ± 7.3 | 36.7 ± 0.8 | 31.5 ± 3.7 | 2.28 |
| bLinS-L72F | 2.7 ± 1.6 | ND | 24.3 ± 11.1 | 8.3 ± 9.4 | ND |
| bLinS-L72M | 429.1 ± 12.1 | 43.8 ± 1.9 | 26.5 ± 4.0 | 6.2 ± 1.6 | 9.80 |
| bLinS-L72I | 1.1 ± 0.2 | ND | 13.9 ± 6.3 | 1.7 ± 2.0 | ND |
| bLinS-L72N | 0.03 ± 0.05 | ND | 20.9 ± 12.3 | 5.7 ± 2.8 | ND |
| bLinS-L72Q | 0.2 ± 0.1 | ND | 19.1 ± 7.1 | 1.7 ± 0.2 | ND |
| bLinS-V214F | ND | ND | 7.7 ± 11.4 |  | ND |
| bLinS-V214L | 49.2 ± 4.8 | 2.1 ± 0.8 | 79.1 ± 8.2 | 2.0 ± 0.4 | 23.43 |
| bLinS-V214I | 265.3 ± 39.2 | 109.7 ± 52.1 | 6.8 ± 1.5 | 9.3 ± 10.8 | 2.42 |
| bLinS-V214M | 0.9 ± 0.7 | ND | 6.1 ± 6.7 | 1.7 ± 1.8 | ND |
| bLinS-V214S | 0.2 ± 0.1 | ND | 21.8 ± 9.1 | 1.8 ± 0.9 | ND |
| bLinS-L72M-V214I | 1054.0 ± 245.2 | 379.0 ± 134.3 | 13.1 ± 4.2 | 9.9 ± 5.2 | 2.78 |
| bLinS-L72M-V214L | 192.6 ± 86.5 | 5.8 ± 3.5 | 38.4 ± 22.4 | 21.9 ± 30.3 | 33.20 |

Figure 14

SEQUENCE LISTING

```
<160> NUMBER OF SEQ ID NOS: 39

<210> SEQ ID NO 1
<211> LENGTH: 329
<212> TYPE: PRT
<213> ORGANISM: Artificial Sequence
<220> FEATURE:
<223> OTHER INFORMATION: Linalool synthase from Streptomyces
      clavuligerus (L72 and V214 shaded)

<400> SEQUENCE: 1

Met Gln Glu Phe Glu Phe Ala Val Pro Ala Pro Ser Arg Val Ser Pro
1               5                   10                  15

Asp Leu Ala Arg Ala Arg Ala Arg His Leu Asp Trp Val His Ala Met
            20                  25                  30

Asp Leu Val Arg Gly Glu Glu Ala Arg Arg Tyr Glu Phe Ser Cys
        35                  40                  45

Val Ala Asp Ile Gly Ala Tyr Gly Tyr Pro His Ala Thr Gly Ala Asp
    50                  55                  60

Leu Asp Leu Cys Val Asp Val Leu Gly Trp Thr Phe Leu Phe Asp Asp
65                  70                  75                  80

Gln Phe Asp Ala Gly Asp Gly Arg Glu Arg Asp Ala Leu Ala Val Cys
                85                  90                  95

Ala Glu Leu Thr Asp Leu Leu Trp Lys Gly Thr Ala Ala Thr Ala Ala
            100                 105                 110

Ser Pro Pro Ile Val Val Ala Phe Ser Asp Cys Trp Glu Arg Met Arg
        115                 120                 125

Ala Gly Met Ser Asp Ala Trp Arg Arg Arg Thr Val His Glu Trp Val
    130                 135                 140

Asp Tyr Leu Ala Gly Trp Pro Thr Lys Leu Ala Asp Arg Ala His Gly
145                 150                 155                 160

Ala Val Leu Asp Pro Ala Ala His Leu Arg Ala Arg His Arg Thr Ile
                165                 170                 175

Cys Cys Arg Pro Leu Phe Ala Leu Ala Glu Arg Val Gly Gly Tyr Glu
            180                 185                 190
```

```
Val Pro Arg Arg Ala Trp His Ser Ser Arg Leu Asp Gly Met Arg Phe
            195                 200                 205

Thr Thr Ser Asp Ala Val Ile Gly Met Asn Glu Leu His Ser Phe Glu
    210                 215                 220

Lys Asp Arg Ala Gln Gly His Ala Asn Leu Val Leu Ser Leu Val His
225                 230                 235                 240

His Gly Gly Leu Thr Gly Pro Glu Ala Val Thr Arg Val Cys Asp Leu
                245                 250                 255

Val Gln Gly Ser Ile Glu Ser Phe Leu Arg Leu Arg Ser Gly Leu Pro
                260                 265                 270

Glu Leu Gly Arg Ala Leu Gly Val Gly Ala Val Leu Asp Arg Tyr
                275                 280                 285

Ala Asp Ala Leu Ser Ala Phe Cys Arg Gly Tyr His Asp Trp Gly Arg
    290                 295                 300

Gly Ala Ser Arg Tyr Thr Thr Arg Asp His Pro Gly Asp Leu Gly Leu
305                 310                 315                 320

Glu Asn Leu Val Ala Arg Ser Ser Gly
                325

<210> SEQ ID NO 2
<211> LENGTH: 329
<212> TYPE: PRT
<213> ORGANISM: Artificial Sequence
<220> FEATURE:
<223> OTHER INFORMATION: Linalool synthase variant bLinS-L72M

<400> SEQUENCE: 2

Met Gln Glu Phe Glu Phe Ala Val Pro Ala Pro Ser Arg Val Ser Pro
1               5                   10                  15

Asp Leu Ala Arg Ala Arg Ala Arg His Leu Asp Trp Val His Ala Met
                20                  25                  30

Asp Leu Val Arg Gly Glu Glu Ala Arg Arg Tyr Glu Phe Ser Cys
            35                  40                  45

Val Ala Asp Ile Gly Ala Tyr Gly Tyr Pro His Ala Thr Gly Ala Asp
    50                  55                  60

Leu Asp Leu Cys Val Asp Val Met Gly Trp Thr Phe Leu Phe Asp Asp
65                  70                  75                  80

Gln Phe Asp Ala Gly Asp Gly Arg Glu Arg Asp Ala Leu Ala Val Cys
                85                  90                  95

Ala Glu Leu Thr Asp Leu Leu Trp Lys Gly Thr Ala Ala Thr Ala Ala
                100                 105                 110

Ser Pro Pro Ile Val Val Ala Phe Ser Asp Cys Trp Glu Arg Met Arg
            115                 120                 125

Ala Gly Met Ser Asp Ala Trp Arg Arg Thr Val His Glu Trp Val
            130                 135                 140

Asp Tyr Leu Ala Gly Trp Pro Thr Lys Leu Ala Asp Arg Ala His Gly
145                 150                 155                 160

Ala Val Leu Asp Pro Ala Ala His Leu Arg Ala Arg His Arg Thr Ile
                165                 170                 175

Cys Cys Arg Pro Leu Phe Ala Leu Ala Glu Arg Val Gly Gly Tyr Glu
            180                 185                 190

Val Pro Arg Arg Ala Trp His Ser Ser Arg Leu Asp Gly Met Arg Phe
            195                 200                 205

Thr Thr Ser Asp Ala Val Ile Gly Met Asn Glu Leu His Ser Phe Glu
    210                 215                 220
```

```
Lys Asp Arg Ala Gln Gly His Ala Asn Leu Val Leu Ser Leu Val His
225                 230                 235                 240

His Gly Gly Leu Thr Gly Pro Glu Ala Val Thr Arg Val Cys Asp Leu
                245                 250                 255

Val Gln Gly Ser Ile Glu Ser Phe Leu Arg Leu Arg Ser Gly Leu Pro
            260                 265                 270

Glu Leu Gly Arg Ala Leu Gly Val Glu Gly Ala Val Leu Asp Arg Tyr
            275                 280                 285

Ala Asp Ala Leu Ser Ala Phe Cys Arg Gly Tyr His Asp Trp Gly Arg
            290                 295                 300

Gly Ala Ser Arg Tyr Thr Thr Arg Asp His Pro Gly Asp Leu Gly Leu
305                 310                 315                 320

Glu Asn Leu Val Ala Arg Ser Ser Gly
                325
```

<210> SEQ ID NO 3
<211> LENGTH: 329
<212> TYPE: PRT
<213> ORGANISM: Artificial Sequence
<220> FEATURE:
<223> OTHER INFORMATION: Linalool synthase variant bLinS-V214L

<400> SEQUENCE: 3

```
Met Gln Glu Phe Glu Phe Ala Val Pro Ala Pro Ser Arg Val Ser Pro
1               5                   10                  15

Asp Leu Ala Arg Ala Arg Ala Arg His Leu Asp Trp Val His Ala Met
                20                  25                  30

Asp Leu Val Arg Gly Glu Glu Ala Arg Arg Arg Tyr Glu Phe Ser Cys
            35                  40                  45

Val Ala Asp Ile Gly Ala Tyr Gly Tyr Pro His Ala Thr Gly Ala Asp
        50                  55                  60

Leu Asp Leu Cys Val Asp Val Leu Gly Trp Thr Phe Leu Phe Asp Asp
65                  70                  75                  80

Gln Phe Asp Ala Gly Asp Gly Arg Glu Arg Asp Ala Leu Ala Val Cys
                85                  90                  95

Ala Glu Leu Thr Asp Leu Leu Trp Lys Gly Thr Ala Ala Thr Ala Ala
                100                 105                 110

Ser Pro Pro Ile Val Val Ala Phe Ser Asp Cys Trp Glu Arg Met Arg
            115                 120                 125

Ala Gly Met Ser Asp Ala Trp Arg Arg Arg Thr Val His Glu Trp Val
            130                 135                 140

Asp Tyr Leu Ala Gly Trp Pro Thr Lys Leu Ala Asp Arg Ala His Gly
145                 150                 155                 160

Ala Val Leu Asp Pro Ala Ala His Leu Arg Ala Arg His Arg Thr Ile
                165                 170                 175

Cys Cys Arg Pro Leu Phe Ala Leu Ala Glu Arg Val Gly Gly Tyr Glu
            180                 185                 190

Val Pro Arg Arg Ala Trp His Ser Ser Arg Leu Asp Gly Met Arg Phe
            195                 200                 205

Thr Thr Ser Asp Ala Leu Ile Gly Met Asn Glu Leu His Ser Phe Glu
            210                 215                 220

Lys Asp Arg Ala Gln Gly His Ala Asn Leu Val Leu Ser Leu Val His
225                 230                 235                 240

His Gly Gly Leu Thr Gly Pro Glu Ala Val Thr Arg Val Cys Asp Leu
                245                 250                 255
```

```
Val Gln Gly Ser Ile Glu Ser Phe Leu Arg Leu Arg Ser Gly Leu Pro
            260                 265                 270

Glu Leu Gly Arg Ala Leu Gly Val Glu Gly Ala Val Leu Asp Arg Tyr
        275                 280                 285

Ala Asp Ala Leu Ser Ala Phe Cys Arg Gly Tyr His Asp Trp Gly Arg
290                 295                 300

Gly Ala Ser Arg Tyr Thr Thr Arg Asp His Pro Gly Asp Leu Gly Leu
305                 310                 315                 320

Glu Asn Leu Val Ala Arg Ser Ser Gly
                325

<210> SEQ ID NO 4
<211> LENGTH: 329
<212> TYPE: PRT
<213> ORGANISM: Artificial Sequence
<220> FEATURE:
<223> OTHER INFORMATION: Linalool synthase variant bLinS-V214I

<400> SEQUENCE: 4

Met Gln Glu Phe Glu Phe Ala Val Pro Ala Pro Ser Arg Val Ser Pro
1               5                   10                  15

Asp Leu Ala Arg Ala Arg Ala Arg His Leu Asp Trp Val His Ala Met
            20                  25                  30

Asp Leu Val Arg Gly Glu Glu Ala Arg Arg Tyr Glu Phe Ser Cys
        35                  40                  45

Val Ala Asp Ile Gly Ala Tyr Gly Tyr Pro His Ala Thr Gly Ala Asp
    50                  55                  60

Leu Asp Leu Cys Val Asp Val Leu Gly Trp Thr Phe Leu Phe Asp Asp
65                  70                  75                  80

Gln Phe Asp Ala Gly Asp Gly Arg Glu Arg Asp Ala Leu Ala Val Cys
                85                  90                  95

Ala Glu Leu Thr Asp Leu Leu Trp Lys Gly Thr Ala Ala Thr Ala Ala
            100                 105                 110

Ser Pro Pro Ile Val Val Ala Phe Ser Asp Cys Trp Glu Arg Met Arg
        115                 120                 125

Ala Gly Met Ser Asp Ala Trp Arg Arg Thr Val His Glu Trp Val
130                 135                 140

Asp Tyr Leu Ala Gly Trp Pro Thr Lys Leu Ala Asp Arg Ala His Gly
145                 150                 155                 160

Ala Val Leu Asp Pro Ala Ala His Leu Arg Ala Arg His Arg Thr Ile
                165                 170                 175

Cys Cys Arg Pro Leu Phe Ala Leu Ala Glu Arg Val Gly Gly Tyr Glu
            180                 185                 190

Val Pro Arg Arg Ala Trp His Ser Ser Arg Leu Asp Gly Met Arg Phe
        195                 200                 205

Thr Thr Ser Asp Ala Ile Ile Gly Met Asn Glu Leu His Ser Phe Glu
    210                 215                 220

Lys Asp Arg Ala Gln Gly His Ala Asn Leu Val Leu Ser Leu Val His
225                 230                 235                 240

His Gly Gly Leu Thr Gly Pro Glu Ala Val Thr Arg Val Cys Asp Leu
                245                 250                 255

Val Gln Gly Ser Ile Glu Ser Phe Leu Arg Leu Arg Ser Gly Leu Pro
            260                 265                 270

Glu Leu Gly Arg Ala Leu Gly Val Glu Gly Ala Val Leu Asp Arg Tyr
        275                 280                 285
```

Ala Asp Ala Leu Ser Ala Phe Cys Arg Gly Tyr His Asp Trp Gly Arg
    290                 295                 300

Gly Ala Ser Arg Tyr Thr Thr Arg Asp His Pro Gly Asp Leu Gly Leu
305                 310                 315                 320

Glu Asn Leu Val Ala Arg Ser Ser Gly
                325

<210> SEQ ID NO 5
<211> LENGTH: 329
<212> TYPE: PRT
<213> ORGANISM: Artificial Sequence
<220> FEATURE:
<223> OTHER INFORMATION: Linalool synthase variant bLinS-L72M-V214I

<400> SEQUENCE: 5

Met Gln Glu Phe Glu Phe Ala Val Pro Ala Pro Ser Arg Val Ser Pro
1               5                   10                  15

Asp Leu Ala Arg Ala Arg Ala Arg His Leu Asp Trp Val His Ala Met
                20                  25                  30

Asp Leu Val Arg Gly Glu Glu Ala Arg Arg Tyr Glu Phe Ser Cys
            35                  40                  45

Val Ala Asp Ile Gly Ala Tyr Gly Tyr Pro His Ala Thr Gly Ala Asp
    50                  55                  60

Leu Asp Leu Cys Val Asp Val Met Gly Trp Thr Phe Leu Phe Asp Asp
65                  70                  75                  80

Gln Phe Asp Ala Gly Asp Gly Arg Glu Arg Asp Ala Leu Ala Val Cys
                85                  90                  95

Ala Glu Leu Thr Asp Leu Leu Trp Lys Gly Thr Ala Ala Thr Ala Ala
                100                 105                 110

Ser Pro Pro Ile Val Val Ala Phe Ser Asp Cys Trp Glu Arg Met Arg
            115                 120                 125

Ala Gly Met Ser Asp Ala Trp Arg Arg Arg Thr Val His Glu Trp Val
    130                 135                 140

Asp Tyr Leu Ala Gly Trp Pro Thr Lys Leu Ala Asp Arg Ala His Gly
145                 150                 155                 160

Ala Val Leu Asp Pro Ala Ala His Leu Arg Ala Arg His Arg Thr Ile
                165                 170                 175

Cys Cys Arg Pro Leu Phe Ala Leu Ala Glu Arg Val Gly Gly Tyr Glu
            180                 185                 190

Val Pro Arg Arg Ala Trp His Ser Ser Arg Leu Asp Gly Met Arg Phe
    195                 200                 205

Thr Thr Ser Asp Ala Ile Ile Gly Met Asn Glu Leu His Ser Phe Glu
210                 215                 220

Lys Asp Arg Ala Gln Gly His Ala Asn Leu Val Leu Ser Leu Val His
225                 230                 235                 240

His Gly Gly Leu Thr Gly Pro Glu Ala Val Thr Arg Val Cys Asp Leu
                245                 250                 255

Val Gln Gly Ser Ile Glu Ser Phe Leu Arg Leu Arg Ser Gly Leu Pro
            260                 265                 270

Glu Leu Gly Arg Ala Leu Gly Val Glu Gly Ala Val Leu Asp Arg Tyr
    275                 280                 285

Ala Asp Ala Leu Ser Ala Phe Cys Arg Gly Tyr His Asp Trp Gly Arg
    290                 295                 300

Gly Ala Ser Arg Tyr Thr Thr Arg Asp His Pro Gly Asp Leu Gly Leu
305                 310                 315                 320

Glu Asn Leu Val Ala Arg Ser Ser Gly
            325

<210> SEQ ID NO 6
<211> LENGTH: 329
<212> TYPE: PRT
<213> ORGANISM: Artificial Sequence
<220> FEATURE:
<223> OTHER INFORMATION: Linalool synthase variant bLinS-L72M-V214L

<400> SEQUENCE: 6

Met Gln Glu Phe Glu Phe Ala Val Pro Ala Pro Ser Arg Val Ser Pro
1               5                   10                  15

Asp Leu Ala Arg Ala Arg Ala Arg His Leu Asp Trp Val His Ala Met
            20                  25                  30

Asp Leu Val Arg Gly Glu Glu Ala Arg Arg Tyr Glu Phe Ser Cys
        35                  40                  45

Val Ala Asp Ile Gly Ala Tyr Gly Tyr Pro His Ala Thr Gly Ala Asp
    50                  55                  60

Leu Asp Leu Cys Val Asp Val Met Gly Trp Thr Phe Leu Phe Asp Asp
65                  70                  75                  80

Gln Phe Asp Ala Gly Asp Gly Arg Glu Arg Asp Ala Leu Ala Val Cys
                85                  90                  95

Ala Glu Leu Thr Asp Leu Leu Trp Lys Gly Thr Ala Ala Thr Ala Ala
            100                 105                 110

Ser Pro Pro Ile Val Val Ala Phe Ser Asp Cys Trp Glu Arg Met Arg
        115                 120                 125

Ala Gly Met Ser Asp Ala Trp Arg Arg Thr Val His Glu Trp Val
    130                 135                 140

Asp Tyr Leu Ala Gly Trp Pro Thr Lys Leu Ala Asp Arg Ala His Gly
145                 150                 155                 160

Ala Val Leu Asp Pro Ala Ala His Leu Arg Ala Arg His Arg Thr Ile
                165                 170                 175

Cys Cys Arg Pro Leu Phe Ala Leu Ala Glu Arg Val Gly Gly Tyr Glu
            180                 185                 190

Val Pro Arg Arg Ala Trp His Ser Ser Arg Leu Asp Gly Met Arg Phe
        195                 200                 205

Thr Thr Ser Asp Ala Leu Ile Gly Met Asn Glu Leu His Ser Phe Glu
    210                 215                 220

Lys Asp Arg Ala Gln Gly His Ala Asn Leu Val Leu Ser Leu Val His
225                 230                 235                 240

His Gly Gly Leu Thr Gly Pro Glu Ala Val Thr Arg Val Cys Asp Leu
                245                 250                 255

Val Gln Gly Ser Ile Glu Ser Phe Leu Arg Leu Arg Ser Gly Leu Pro
            260                 265                 270

Glu Leu Gly Arg Ala Leu Gly Val Glu Gly Ala Val Leu Asp Arg Tyr
        275                 280                 285

Ala Asp Ala Leu Ser Ala Phe Cys Arg Gly Tyr His Asp Trp Gly Arg
    290                 295                 300

Gly Ala Ser Arg Tyr Thr Thr Arg Asp His Pro Gly Asp Leu Gly Leu
305                 310                 315                 320

Glu Asn Leu Val Ala Arg Ser Ser Gly
            325

<210> SEQ ID NO 7

```
<211> LENGTH: 355
<212> TYPE: PRT
<213> ORGANISM: Artificial Sequence
<220> FEATURE:
<223> OTHER INFORMATION: Linalool synthase from Streptomyces
      clavuligerus with leader sequence

<400> SEQUENCE: 7
```

Met Lys His His His His His Pro Met Ser Asp Tyr Asp Ile Pro
1               5                   10                  15

Thr Thr Glu Asn Leu Tyr Phe Gln Gly Ala Met Gln Glu Phe Glu Phe
            20                  25                  30

Ala Val Pro Ala Pro Ser Arg Val Ser Pro Asp Leu Ala Arg Ala Arg
            35                  40                  45

Ala Arg His Leu Asp Trp Val His Ala Met Asp Leu Val Arg Gly Glu
        50                  55                  60

Glu Ala Arg Arg Arg Tyr Glu Phe Ser Cys Val Ala Asp Ile Gly Ala
65                  70                  75                  80

Tyr Gly Tyr Pro His Ala Thr Gly Ala Asp Leu Asp Leu Cys Val Asp
                85                  90                  95

Val Leu Gly Trp Thr Phe Leu Phe Asp Asp Gln Phe Asp Ala Gly Asp
            100                 105                 110

Gly Arg Glu Arg Asp Ala Leu Ala Val Cys Ala Glu Leu Thr Asp Leu
        115                 120                 125

Leu Trp Lys Gly Thr Ala Ala Thr Ala Ala Ser Pro Pro Ile Val Val
130                 135                 140

Ala Phe Ser Asp Cys Trp Glu Arg Met Arg Ala Gly Met Ser Asp Ala
145                 150                 155                 160

Trp Arg Arg Arg Thr Val His Glu Trp Val Asp Tyr Leu Ala Gly Trp
                165                 170                 175

Pro Thr Lys Leu Ala Asp Arg Ala His Gly Ala Val Leu Asp Pro Ala
            180                 185                 190

Ala His Leu Arg Ala Arg His Arg Thr Ile Cys Cys Arg Pro Leu Phe
        195                 200                 205

Ala Leu Ala Glu Arg Val Gly Gly Tyr Glu Val Pro Arg Arg Ala Trp
210                 215                 220

His Ser Ser Arg Leu Asp Gly Met Arg Phe Thr Thr Ser Asp Ala Val
225                 230                 235                 240

Ile Gly Met Asn Glu Leu His Ser Phe Glu Lys Asp Arg Ala Gln Gly
                245                 250                 255

His Ala Asn Leu Val Leu Ser Leu Val His His Gly Gly Leu Thr Gly
            260                 265                 270

Pro Glu Ala Val Thr Arg Val Cys Asp Leu Val Gln Gly Ser Ile Glu
        275                 280                 285

Ser Phe Leu Arg Leu Arg Ser Gly Leu Pro Glu Leu Gly Arg Ala Leu
290                 295                 300

Gly Val Glu Gly Ala Val Leu Asp Arg Tyr Ala Asp Ala Leu Ser Ala
305                 310                 315                 320

Phe Cys Arg Gly Tyr His Asp Trp Gly Arg Gly Ala Ser Arg Tyr Thr
                325                 330                 335

Thr Arg Asp His Pro Gly Asp Leu Gly Leu Glu Asn Leu Val Ala Arg
            340                 345                 350

Ser Ser Gly
        355

<210> SEQ ID NO 8
<211> LENGTH: 355
<212> TYPE: PRT
<213> ORGANISM: Artificial Sequence
<220> FEATURE:
<223> OTHER INFORMATION: Linalool synthase variant bLinS-L72M with leader sequence

<400> SEQUENCE: 8

```
Met Lys His His His His His Pro Met Ser Asp Tyr Asp Ile Pro
1               5                   10                  15

Thr Thr Glu Asn Leu Tyr Phe Gln Gly Ala Met Gln Glu Phe Glu
            20                  25                  30

Ala Val Pro Ala Pro Ser Arg Val Ser Pro Asp Leu Ala Arg Ala
        35                  40                  45

Ala Arg His Leu Asp Trp Val His Ala Met Asp Leu Val Arg Gly Glu
    50                  55                  60

Glu Ala Arg Arg Arg Tyr Glu Phe Ser Cys Val Ala Asp Ile Gly Ala
65                  70                  75                  80

Tyr Gly Tyr Pro His Ala Thr Gly Ala Asp Leu Asp Leu Cys Val Asp
                85                  90                  95

Val Met Gly Trp Thr Phe Leu Phe Asp Asp Gln Phe Asp Ala Gly Asp
            100                 105                 110

Gly Arg Glu Arg Asp Ala Leu Ala Val Cys Ala Glu Leu Thr Asp Leu
        115                 120                 125

Leu Trp Lys Gly Thr Ala Ala Thr Ala Ala Ser Pro Pro Ile Val Val
    130                 135                 140

Ala Phe Ser Asp Cys Trp Glu Arg Met Arg Ala Gly Met Ser Asp Ala
145                 150                 155                 160

Trp Arg Arg Arg Thr Val His Glu Trp Val Asp Tyr Leu Ala Gly Trp
                165                 170                 175

Pro Thr Lys Leu Ala Asp Arg Ala His Gly Ala Val Leu Asp Pro Ala
            180                 185                 190

Ala His Leu Arg Ala Arg His Arg Thr Ile Cys Cys Arg Pro Leu Phe
        195                 200                 205

Ala Leu Ala Glu Arg Val Gly Gly Tyr Glu Val Pro Arg Arg Ala Trp
    210                 215                 220

His Ser Ser Arg Leu Asp Gly Met Arg Phe Thr Thr Ser Asp Ala Val
225                 230                 235                 240

Ile Gly Met Asn Glu Leu His Ser Phe Glu Lys Asp Arg Ala Gln Gly
                245                 250                 255

His Ala Asn Leu Val Leu Ser Leu Val His His Gly Gly Leu Thr Gly
            260                 265                 270

Pro Glu Ala Val Thr Arg Val Cys Asp Leu Val Gln Gly Ser Ile Glu
        275                 280                 285

Ser Phe Leu Arg Leu Arg Ser Gly Leu Pro Glu Leu Gly Arg Ala Leu
    290                 295                 300

Gly Val Glu Gly Ala Val Leu Asp Arg Tyr Ala Asp Ala Leu Ser Ala
305                 310                 315                 320

Phe Cys Arg Gly Tyr His Asp Trp Gly Arg Gly Ala Ser Arg Tyr Thr
                325                 330                 335

Thr Arg Asp His Pro Gly Asp Leu Gly Leu Glu Asn Leu Val Ala Arg
            340                 345                 350

Ser Ser Gly
        355
```

<210> SEQ ID NO 9
<211> LENGTH: 355
<212> TYPE: PRT
<213> ORGANISM: Artificial Sequence
<220> FEATURE:
<223> OTHER INFORMATION: Linalool synthase variant bLinS-V214L with leader sequence

<400> SEQUENCE: 9

```
Met Lys His His His His His Pro Met Ser Asp Tyr Asp Ile Pro
 1               5                  10                  15

Thr Thr Glu Asn Leu Tyr Phe Gln Gly Ala Met Gln Glu Phe Glu Phe
            20                  25                  30

Ala Val Pro Ala Pro Ser Arg Val Ser Pro Asp Leu Ala Arg Ala Arg
        35                  40                  45

Ala Arg His Leu Asp Trp Val His Ala Met Asp Leu Val Arg Gly Glu
    50                  55                  60

Glu Ala Arg Arg Arg Tyr Glu Phe Ser Cys Val Ala Asp Ile Gly Ala
65                  70                  75                  80

Tyr Gly Tyr Pro His Ala Thr Gly Ala Asp Leu Asp Leu Cys Val Asp
                85                  90                  95

Val Leu Gly Trp Thr Phe Leu Phe Asp Asp Gln Phe Asp Ala Gly Asp
            100                 105                 110

Gly Arg Glu Arg Asp Ala Leu Ala Val Cys Ala Glu Leu Thr Asp Leu
        115                 120                 125

Leu Trp Lys Gly Thr Ala Ala Thr Ala Ala Ser Pro Pro Ile Val Val
    130                 135                 140

Ala Phe Ser Asp Cys Trp Glu Arg Met Arg Ala Gly Met Ser Asp Ala
145                 150                 155                 160

Trp Arg Arg Arg Thr Val His Glu Trp Val Asp Tyr Leu Ala Gly Trp
                165                 170                 175

Pro Thr Lys Leu Ala Asp Arg Ala His Gly Ala Val Leu Asp Pro Ala
            180                 185                 190

Ala His Leu Arg Ala Arg His Arg Thr Ile Cys Cys Arg Pro Leu Phe
        195                 200                 205

Ala Leu Ala Glu Arg Val Gly Gly Tyr Glu Val Pro Arg Arg Ala Trp
    210                 215                 220

His Ser Ser Arg Leu Asp Gly Met Arg Phe Thr Thr Ser Asp Ala Leu
225                 230                 235                 240

Ile Gly Met Asn Glu Leu His Ser Phe Glu Lys Asp Arg Ala Gln Gly
                245                 250                 255

His Ala Asn Leu Val Leu Ser Leu Val His His Gly Gly Leu Thr Gly
            260                 265                 270

Pro Glu Ala Val Thr Arg Val Cys Asp Leu Val Gln Gly Ser Ile Glu
        275                 280                 285

Ser Phe Leu Arg Leu Arg Ser Gly Leu Pro Glu Leu Gly Arg Ala Leu
    290                 295                 300

Gly Val Glu Gly Ala Val Leu Asp Arg Tyr Ala Asp Ala Leu Ser Ala
305                 310                 315                 320

Phe Cys Arg Gly Tyr His Asp Trp Gly Arg Gly Ala Ser Arg Tyr Thr
                325                 330                 335

Thr Arg Asp His Pro Gly Asp Leu Gly Leu Glu Asn Leu Val Ala Arg
            340                 345                 350

Ser Ser Gly
        355
```

```
<210> SEQ ID NO 10
<211> LENGTH: 355
<212> TYPE: PRT
<213> ORGANISM: Artificial Sequence
<220> FEATURE:
<223> OTHER INFORMATION: Linalool synthase variant bLinS-V214I with
      leader sequence

<400> SEQUENCE: 10

Met Lys His His His His His His Pro Met Ser Asp Tyr Asp Ile Pro
1               5                   10                  15

Thr Thr Glu Asn Leu Tyr Phe Gln Gly Ala Met Gln Glu Phe Glu Phe
            20                  25                  30

Ala Val Pro Ala Pro Ser Arg Val Ser Pro Asp Leu Ala Arg Ala Arg
        35                  40                  45

Ala Arg His Leu Asp Trp Val His Ala Met Asp Leu Val Arg Gly Glu
    50                  55                  60

Glu Ala Arg Arg Arg Tyr Glu Phe Ser Cys Val Ala Asp Ile Gly Ala
65                  70                  75                  80

Tyr Gly Tyr Pro His Ala Thr Gly Ala Asp Leu Asp Leu Cys Val Asp
                85                  90                  95

Val Leu Gly Trp Thr Phe Leu Phe Asp Asp Gln Phe Asp Ala Gly Asp
            100                 105                 110

Gly Arg Glu Arg Asp Ala Leu Ala Val Cys Ala Glu Leu Thr Asp Leu
        115                 120                 125

Leu Trp Lys Gly Thr Ala Ala Thr Ala Ala Ser Pro Pro Ile Val Val
    130                 135                 140

Ala Phe Ser Asp Cys Trp Glu Arg Met Arg Ala Gly Met Ser Asp Ala
145                 150                 155                 160

Trp Arg Arg Arg Thr Val His Glu Trp Val Asp Tyr Leu Ala Gly Trp
                165                 170                 175

Pro Thr Lys Leu Ala Asp Arg Ala His Gly Ala Val Leu Asp Pro Ala
            180                 185                 190

Ala His Leu Arg Ala Arg His Arg Thr Ile Cys Cys Arg Pro Leu Phe
        195                 200                 205

Ala Leu Ala Glu Arg Val Gly Gly Tyr Glu Val Pro Arg Arg Ala Trp
    210                 215                 220

His Ser Ser Arg Leu Asp Gly Met Arg Phe Thr Thr Ser Asp Ala Ile
225                 230                 235                 240

Ile Gly Met Asn Glu Leu His Ser Phe Glu Lys Asp Arg Ala Gln Gly
                245                 250                 255

His Ala Asn Leu Val Leu Ser Leu Val His His Gly Gly Leu Thr Gly
            260                 265                 270

Pro Glu Ala Val Thr Arg Val Cys Asp Leu Val Gln Gly Ser Ile Glu
        275                 280                 285

Ser Phe Leu Arg Leu Arg Ser Gly Leu Pro Glu Leu Gly Arg Ala Leu
    290                 295                 300

Gly Val Glu Gly Ala Val Leu Asp Arg Tyr Ala Asp Ala Leu Ser Ala
305                 310                 315                 320

Phe Cys Arg Gly Tyr His Asp Trp Gly Arg Gly Ala Ser Arg Tyr Thr
                325                 330                 335

Thr Arg Asp His Pro Gly Asp Leu Gly Leu Glu Asn Leu Val Ala Arg
            340                 345                 350

Ser Ser Gly
```

```
<210> SEQ ID NO 11
<211> LENGTH: 355
<212> TYPE: PRT
<213> ORGANISM: Artificial Sequence
<220> FEATURE:
<223> OTHER INFORMATION: Linalool synthase variant bLinS-L72M-V214I with
      leader sequence

<400> SEQUENCE: 11

Met Lys His His His His His His Pro Met Ser Asp Tyr Asp Ile Pro
1               5                   10                  15

Thr Thr Glu Asn Leu Tyr Phe Gln Gly Ala Met Gln Glu Phe Glu Phe
            20                  25                  30

Ala Val Pro Ala Pro Ser Arg Val Ser Pro Asp Leu Ala Arg Ala Arg
        35                  40                  45

Ala Arg His Leu Asp Trp Val His Ala Met Asp Leu Val Arg Gly Glu
    50                  55                  60

Glu Ala Arg Arg Arg Tyr Glu Phe Ser Cys Val Ala Asp Ile Gly Ala
65                  70                  75                  80

Tyr Gly Tyr Pro His Ala Thr Gly Ala Asp Leu Asp Leu Cys Val Asp
                85                  90                  95

Val Met Gly Trp Thr Phe Leu Phe Asp Asp Gln Phe Asp Ala Gly Asp
            100                 105                 110

Gly Arg Glu Arg Asp Ala Leu Ala Val Cys Ala Glu Leu Thr Asp Leu
        115                 120                 125

Leu Trp Lys Gly Thr Ala Ala Thr Ala Ala Ser Pro Pro Ile Val Val
    130                 135                 140

Ala Phe Ser Asp Cys Trp Glu Arg Met Arg Ala Gly Met Ser Asp Ala
145                 150                 155                 160

Trp Arg Arg Arg Thr Val His Glu Trp Val Asp Tyr Leu Ala Gly Trp
                165                 170                 175

Pro Thr Lys Leu Ala Asp Arg Ala His Gly Ala Val Leu Asp Pro Ala
            180                 185                 190

Ala His Leu Arg Ala Arg His Arg Thr Ile Cys Cys Arg Pro Leu Phe
        195                 200                 205

Ala Leu Ala Glu Arg Val Gly Gly Tyr Glu Val Pro Arg Arg Ala Trp
    210                 215                 220

His Ser Ser Arg Leu Asp Gly Met Arg Phe Thr Thr Ser Asp Ala Ile
225                 230                 235                 240

Ile Gly Met Asn Glu Leu His Ser Phe Glu Lys Asp Arg Ala Gln Gly
                245                 250                 255

His Ala Asn Leu Val Leu Ser Leu Val His His Gly Gly Leu Thr Gly
            260                 265                 270

Pro Glu Ala Val Thr Arg Val Cys Asp Leu Val Gln Gly Ser Ile Glu
        275                 280                 285

Ser Phe Leu Arg Leu Arg Ser Gly Leu Pro Glu Leu Gly Arg Ala Leu
    290                 295                 300

Gly Val Glu Gly Ala Val Leu Asp Arg Tyr Ala Asp Ala Leu Ser Ala
305                 310                 315                 320

Phe Cys Arg Gly Tyr His Asp Trp Gly Arg Gly Ala Ser Arg Tyr Thr
                325                 330                 335

Thr Arg Asp His Pro Gly Asp Leu Gly Leu Glu Asn Leu Val Ala Arg
            340                 345                 350
```

```
Ser Ser Gly
        355
```

<210> SEQ ID NO 12
<211> LENGTH: 355
<212> TYPE: PRT
<213> ORGANISM: Artificial Sequence
<220> FEATURE:
<223> OTHER INFORMATION: Linalool synthase variant bLinS-L72M-V214L with
      leader sequence

<400> SEQUENCE: 12

```
Met Lys His His His His His Pro Met Ser Asp Tyr Asp Ile Pro
1               5                   10                  15

Thr Thr Glu Asn Leu Tyr Phe Gln Gly Ala Met Gln Glu Phe Glu Phe
            20                  25                  30

Ala Val Pro Ala Pro Ser Arg Val Ser Pro Asp Leu Ala Arg Ala Arg
        35                  40                  45

Ala Arg His Leu Asp Trp Val His Ala Met Asp Leu Val Arg Gly Glu
    50                  55                  60

Glu Ala Arg Arg Arg Tyr Glu Phe Ser Cys Val Ala Asp Ile Gly Ala
65                  70                  75                  80

Tyr Gly Tyr Pro His Ala Thr Gly Ala Asp Leu Asp Leu Cys Val Asp
                85                  90                  95

Val Met Gly Trp Thr Phe Leu Phe Asp Asp Gln Phe Asp Ala Gly Asp
            100                 105                 110

Gly Arg Glu Arg Asp Ala Leu Ala Val Cys Ala Glu Leu Thr Asp Leu
        115                 120                 125

Leu Trp Lys Gly Thr Ala Ala Thr Ala Ala Ser Pro Pro Ile Val Val
    130                 135                 140

Ala Phe Ser Asp Cys Trp Glu Arg Met Arg Ala Gly Met Ser Asp Ala
145                 150                 155                 160

Trp Arg Arg Arg Thr Val His Glu Trp Val Asp Tyr Leu Ala Gly Trp
                165                 170                 175

Pro Thr Lys Leu Ala Asp Arg Ala His Gly Ala Val Leu Asp Pro Ala
            180                 185                 190

Ala His Leu Arg Ala Arg His Arg Thr Ile Cys Cys Arg Pro Leu Phe
        195                 200                 205

Ala Leu Ala Glu Arg Val Gly Gly Tyr Glu Val Pro Arg Arg Ala Trp
    210                 215                 220

His Ser Ser Arg Leu Asp Gly Met Arg Phe Thr Thr Ser Asp Ala Leu
225                 230                 235                 240

Ile Gly Met Asn Glu Leu His Ser Phe Glu Lys Asp Arg Ala Gln Gly
                245                 250                 255

His Ala Asn Leu Val Leu Ser Leu Val His His Gly Gly Leu Thr Gly
            260                 265                 270

Pro Glu Ala Val Thr Arg Val Cys Asp Leu Val Gln Gly Ser Ile Glu
        275                 280                 285

Ser Phe Leu Arg Leu Arg Ser Gly Leu Pro Glu Leu Gly Arg Ala Leu
    290                 295                 300

Gly Val Glu Gly Ala Val Leu Asp Arg Tyr Ala Asp Ala Leu Ser Ala
305                 310                 315                 320

Phe Cys Arg Gly Tyr His Asp Trp Gly Arg Gly Ala Ser Arg Tyr Thr
                325                 330                 335

Thr Arg Asp His Pro Gly Asp Leu Gly Leu Glu Asn Leu Val Ala Arg
            340                 345                 350
```

Ser Ser Gly
    355

<210> SEQ ID NO 13
<211> LENGTH: 26
<212> TYPE: PRT
<213> ORGANISM: Artificial Sequence
<220> FEATURE:
<223> OTHER INFORMATION: Linalool synthase leader sequence

<400> SEQUENCE: 13

Met Lys His His His His His His Pro Met Ser Asp Tyr Asp Ile Pro
1               5                   10                  15

Thr Thr Glu Asn Leu Tyr Phe Gln Gly Ala
            20                  25

<210> SEQ ID NO 14
<211> LENGTH: 33
<212> TYPE: DNA
<213> ORGANISM: Artificial Sequence
<220> FEATURE:
<223> OTHER INFORMATION: Primer bLinS-L72F_fw

<400> SEQUENCE: 14
ctgtgtgttg atgttttcgg ttggaccttt ctg                     33

<210> SEQ ID NO 15
<211> LENGTH: 33
<212> TYPE: DNA
<213> ORGANISM: Artificial Sequence
<220> FEATURE:
<223> OTHER INFORMATION: Primer bLinS-L72M_fw

<400> SEQUENCE: 15
ctgtgtgttg atgttatggg ttggaccttt ctg                     33

<210> SEQ ID NO 16
<211> LENGTH: 33
<212> TYPE: DNA
<213> ORGANISM: Artificial Sequence
<220> FEATURE:
<223> OTHER INFORMATION: Primer bLinS-L72I_fw

<400> SEQUENCE: 16
ctgtgtgttg atgttattgg ttggaccttt ctg                     33

<210> SEQ ID NO 17
<211> LENGTH: 33
<212> TYPE: DNA
<213> ORGANISM: Artificial Sequence
<220> FEATURE:
<223> OTHER INFORMATION: Primer bLinS-L72N_fw

<400> SEQUENCE: 17
ctgtgtgttg atgttaccgg ttggaccttt ctg                     33

<210> SEQ ID NO 18
<211> LENGTH: 33
<212> TYPE: DNA
<213> ORGANISM: Artificial Sequence
<220> FEATURE:
<223> OTHER INFORMATION: Primer bLinS-L72Q_fw

<400> SEQUENCE: 18
ctgtgtgttg atgttcaggg ttggaccttt ctg                     33

<210> SEQ ID NO 19
<211> LENGTH: 34
<212> TYPE: DNA
<213> ORGANISM: Artificial Sequence
<220> FEATURE:
<223> OTHER INFORMATION: Primer bLinS-T75F_fw

<400> SEQUENCE: 19
gatgttctgg gttggttctt tctgtttgat gatc                            34

<210> SEQ ID NO 20
<211> LENGTH: 34
<212> TYPE: DNA
<213> ORGANISM: Artificial Sequence
<220> FEATURE:
<223> OTHER INFORMATION: Primer bLinS-T75M_fw

<400> SEQUENCE: 20
gatgttctgg gttggatgtt tctgtttgat gatc                            34

<210> SEQ ID NO 21
<211> LENGTH: 31
<212> TYPE: DNA
<213> ORGANISM: Artificial Sequence
<220> FEATURE:
<223> OTHER INFORMATION: Primer bLinS-I176F_fw

<400> SEQUENCE: 21
gctcgccatc gtaccttttg ttgtcgtccg c                               31

<210> SEQ ID NO 22
<211> LENGTH: 31
<212> TYPE: DNA
<213> ORGANISM: Artificial Sequence
<220> FEATURE:
<223> OTHER INFORMATION: Primer bLinS-C177F_fw

<400> SEQUENCE: 22
catcgtacca tttgttttcg tccgctgttt g                               31

<210> SEQ ID NO 23
<211> LENGTH: 31
<212> TYPE: DNA
<213> ORGANISM: Artificial Sequence
<220> FEATURE:
<223> OTHER INFORMATION: Primer bLinS-C178F_fw

<400> SEQUENCE: 23
catcgtacca tttgttttcg tccgctgttt g                               31

<210> SEQ ID NO 24
<211> LENGTH: 31
<212> TYPE: DNA
<213> ORGANISM: Artificial Sequence
<220> FEATURE:
<223> OTHER INFORMATION: Primer bLinS-C178M_fw

<400> SEQUENCE: 24
catcgtacca tttgtatgcg tccgctgttt g                               31

<210> SEQ ID NO 25
<211> LENGTH: 30
<212> TYPE: DNA
<213> ORGANISM: Artificial Sequence
<220> FEATURE:

<223> OTHER INFORMATION: Primer bLinS-V214F_fw

<400> SEQUENCE: 25
ccaccagtga tgcatttatt ggtatgaatg                              30

<210> SEQ ID NO 26
<211> LENGTH: 30
<212> TYPE: DNA
<213> ORGANISM: Artificial Sequence
<220> FEATURE:
<223> OTHER INFORMATION: Primer bLinS-V214L_fw

<400> SEQUENCE: 26
ccaccagtga tgcactgatt ggtatgaatg                              30

<210> SEQ ID NO 27
<211> LENGTH: 30
<212> TYPE: DNA
<213> ORGANISM: Artificial Sequence
<220> FEATURE:
<223> OTHER INFORMATION: Primer bLinS-V214I_fw

<400> SEQUENCE: 27
ccaccagtga tgcaattatt ggtatgaatg                              30

<210> SEQ ID NO 28
<211> LENGTH: 30
<212> TYPE: DNA
<213> ORGANISM: Artificial Sequence
<220> FEATURE:
<223> OTHER INFORMATION: Primer bLinS-V214M_fw

<400> SEQUENCE: 28
ccaccagtga tgcaatgatt ggtatgaatg                              30

<210> SEQ ID NO 29
<211> LENGTH: 30
<212> TYPE: DNA
<213> ORGANISM: Artificial Sequence
<220> FEATURE:
<223> OTHER INFORMATION: Primer bLinS-V214S_fw

<400> SEQUENCE: 29
ccaccagtga tgcaagtatt ggtatgaatg                              30

<210> SEQ ID NO 30
<211> LENGTH: 28
<212> TYPE: DNA
<213> ORGANISM: Artificial Sequence
<220> FEATURE:
<223> OTHER INFORMATION: Primer bLinS-F295W_fw

<400> SEQUENCE: 30
gcactgagcg catggtgtcg tggttatc                                28

<210> SEQ ID NO 31
<211> LENGTH: 28
<212> TYPE: DNA
<213> ORGANISM: Artificial Sequence
<220> FEATURE:
<223> OTHER INFORMATION: Primer bLinS-F295Y_fw

<400> SEQUENCE: 31
gcactgagcg catattgtcg tggttatc                                28

```
<210> SEQ ID NO 32
<211> LENGTH: 5
<212> TYPE: PRT
<213> ORGANISM: Artificial Sequence
<220> FEATURE:
<223> OTHER INFORMATION: aspartate-rich motif
<220> FEATURE:
<221> NAME/KEY: misc_feature
<222> LOCATION: (3)..(4)
<223> OTHER INFORMATION: Xaa can be any naturally occurring amino acid

<400> SEQUENCE: 32

Asp Asp Xaa Xaa Asp
1               5

<210> SEQ ID NO 33
<211> LENGTH: 5
<212> TYPE: PRT
<213> ORGANISM: Artificial Sequence
<220> FEATURE:
<223> OTHER INFORMATION: aspartate-rich motif
<220> FEATURE:
<221> NAME/KEY: misc_feature
<222> LOCATION: (3)..(4)
<223> OTHER INFORMATION: Xaa can be any naturally occurring amino acid

<400> SEQUENCE: 33

Asp Asp Xaa Xaa Glu
1               5

<210> SEQ ID NO 34
<211> LENGTH: 6
<212> TYPE: PRT
<213> ORGANISM: Artificial Sequence
<220> FEATURE:
<223> OTHER INFORMATION: aspartate-rich motif
<220> FEATURE:
<221> NAME/KEY: misc_feature
<222> LOCATION: (3)..(5)
<223> OTHER INFORMATION: Xaa can be any naturally occurring amino acid

<400> SEQUENCE: 34

Asp Asp Xaa Xaa Xaa Asp
1               5

<210> SEQ ID NO 35
<211> LENGTH: 6
<212> TYPE: PRT
<213> ORGANISM: Artificial Sequence
<220> FEATURE:
<223> OTHER INFORMATION: aspartate-rich motif
<220> FEATURE:
<221> NAME/KEY: misc_feature
<222> LOCATION: (3)..(5)
<223> OTHER INFORMATION: Xaa can be any naturally occurring amino acid

<400> SEQUENCE: 35

Asp Asp Xaa Xaa Xaa Glu
1               5

<210> SEQ ID NO 36
<211> LENGTH: 9
<212> TYPE: PRT
<213> ORGANISM: Artificial Sequence
<220> FEATURE:
<223> OTHER INFORMATION: NSE triad
<220> FEATURE:
<221> NAME/KEY: misc_feature
<222> LOCATION: (3)..(4)
<223> OTHER INFORMATION: Xaa can be any naturally occurring amino acid
<220> FEATURE:
```

```
<221> NAME/KEY: misc_feature
<222> LOCATION: (6)..(7)
<223> OTHER INFORMATION: Xaa can be any naturally occurring amino acid

<400> SEQUENCE: 36

Asn Asp Xaa Xaa Ser Xaa Xaa Arg Glu
1               5

<210> SEQ ID NO 37
<211> LENGTH: 9
<212> TYPE: PRT
<213> ORGANISM: Artificial Sequence
<220> FEATURE:
<223> OTHER INFORMATION: NSE triad
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 37

Asn Asp Xaa Xaa Ser Xaa Xaa Arg Asp
1               5

<210> SEQ ID NO 38
<211> LENGTH: 9
<212> TYPE: PRT
<213> ORGANISM: Artificial Sequence
<220> FEATURE:
<223> OTHER INFORMATION: NSE triad
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 38

Asn Asp Xaa Xaa Ser Xaa Xaa Lys Glu
1               5

<210> SEQ ID NO 39
<211> LENGTH: 9
<212> TYPE: PRT
<213> ORGANISM: Artificial Sequence
<220> FEATURE:
<223> OTHER INFORMATION: NSE triad
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 39

Asn Asp Xaa Xaa Ser Xaa Xaa Lys Asp
1               5
```

LINALOOL SYNTHASES

FIELD OF THE INVENTION

The present invention relates to the fields of molecular biology and biotechnology and particularly, although not exclusively, to enzymes for the production of linalool.

BACKGROUND

Terpenoids (also called isoprenoids) are the most abundant and largest class of natural products (>80000). Most commonly found in plants, their biological roles are multitude ranging from species to species communication to intracellular signalling and defence against predatory species. They have a wide range of applications and are used in pharmaceuticals, herbicides, flavourings, fragrances and biofuels. Due to the broad commercial interest for terpenoids, efforts to synthesize them by synthetic biology routes have gathered pace in recent years.

Terpenoid substrates are synthesized from the C5 isoprene building blocks, namely dimethylallyl pyrophosphate (DMAPP) and isopentenyl pyrophosphate (IPP). Combination of DMAPP and IPP can generate substrates of varying carbon lengths, which can then be utilized by terpene synthases/cyclases to produce monoterpenes (C10), sesquiterpenes (C15), diterpenes (C20) and others. For example, geranyl pyrophosphate (GPP), the substrate for making all monoterpenes is synthesized by coupling one molecule each of DMAPP and IPP.

Monoterpene synthases (mTS) are enzymes that use a single C10 substrate molecule geranyl pyrophosphate (GPP) to produce hundreds of diverse monoterpenes. The structure of plant mTS has a two domain architecture: a class I terpenoid cyclase fold C-terminal domain and a relatively small N-terminal domain whose function is unclear. The amino acid sequence variations in the active site combined with conserved residues for GPP recognition results in mTS carrying out some of the most complex reactions in biology leading to the formation of linear, monocyclic and bicyclic terpenoids.

Many monoterpene hydrocarbon scaffolds have been produced in engineered microbes in recent years, using yeast or *E. coli* as a host and employing mTS from plant sources. However, the resulting monoterpene yields are relatively low. Examples of monoterpenoids produced in such systems include geranio, β-myrcene, limonene and pinene.

*E. coli* is the workhorse for recombinant protein production around the world in both academia and industry. This preferred choice is due to the ease of introducing external DNA material into the cell, a fast growth cycle and the use of inexpensive growth media. As mentioned above, for the production of monoterpenes using synthetic biology routes, plant mTS have been utilised. However, the use of such plant mTS has associated disadvantages.

Previous experiments by the inventors have revealed that many plant mTS when overexpressed in *E. coli*, generate mostly insoluble protein i.e., inactive material not suitable for monoterpene biosynthesis. This limited solubility has proved to be a bottleneck in the production of monoterpenes as the majority of the GPP molecules in the host cell are not utilised for the synthesis of monoterpenes, resulting in low product yields/titres. This is particularly the case for biosynthesis of linalool, which is widely used as perfume in cleaning agents. Plant linalool synthases when employed in either yeast or *E. coli* result in very low product titres (0.1-1 mg/$L_{org}^{-1}$).

Two recently characterised bacterial monoterpene cyclases/synthases (mTC/S), a linalool synthase (bLinS) and 1,8-cineole synthase (bCinS) only possess the class I terpenoid cyclase domain and are structurally related to bacterial sesquiterpene synthases (Karuppiah et al., 2017). Whereas bCinS only accepts the GPP substrate, bLinS also accepts farnesyl pyrophosphate (FPP) and produces the monoterpenoid linalool from GPP and the sesquiterpenoid nerolidol from FPP. Additionally, WO 2018/142109 A1 also showed that expression of bacterial monoterpene synthases (mTS) in *E. coli* results in a high yield of monoterpenes.

The presence of geranoid by-products (>10-fold excess) resulting from endogenous *E. coli* activity shows that substrate availability is not the cause of these observed low titres. Lack of robustness also makes plant mTC/S less attractive targets for protein engineering. The use of bLinS, due to its bacterial origin and simpler domain structure, resulted in much higher linalool titres (>350 mg $L_{org}^{-1}$). However, bLinS also accepts FPP and thus resulted in the formation of the sesquiterpene nerolidol as by-product (~30% of total product mixture) when produced in *E. coli* (Karuppiah et al., 2017).

In addition to increased yields, the generation of single, clean products is desirable, as this would require less downstream processing. The current invention addresses this issue.

SUMMARY OF THE INVENTION

The present invention provides linalool synthase variants. The variants preferably comprise an amino acid sequence having one or more amino acid substitutions, the variants producing a greater linalool yield and/or higher linalool: nerolidol ratio compared with the corresponding wild type linalool synthase.

The linalool synthase may comprise an amino acid sequence comprising a substitution corresponding to a residue in SEQ ID NO:1. The linalool synthase may have one, two or more amino acid substitutions.

SEQ ID NO:1 corresponds to the amino acid sequence of wild type *Streptomyces clavuligerus* linalool synthase.

In some embodiments, the linalool synthase comprises an amino acid substitution corresponding to one or more of L72 and V214 relative to SEQ ID NO:1.

In some embodiments, the linalool synthase comprises one or more substitutions corresponding to the following amino acid substitutions relative to SEQ ID NO:1: L72M, L72C, L72S, L72T, L72V, L72A, L72G, V214L, V214I, V214C, V214N, V214Q, V214T, V214A, and V214G.

In some embodiments, the linalool synthase comprises one or more substitutions corresponding to the following amino acid substitutions relative to SEQ ID NO:1: L72M, V214L and V214I.

In some embodiments, the linalool synthase comprises the amino acid substitution L72M relative to SEQ ID NO:1.

In some embodiments, the linalool synthase comprises the amino acid substitution L72C relative to SEQ ID NO:1.

In some embodiments, the linalool synthase comprises the amino acid substitution L72S relative to SEQ ID NO:1.

In some embodiments, the linalool synthase comprises the amino acid substitution L72T relative to SEQ ID NO:1.

In some embodiments, the linalool synthase comprises the amino acid substitution L72V relative to SEQ ID NO:1.

In some embodiments, the linalool synthase comprises the amino acid substitution L72A relative to SEQ ID NO:1.

In some embodiments, the linalool synthase comprises the amino acid substitution L72G relative to SEQ ID NO:1.

In some embodiments, the linalool synthase comprises the amino acid substitution V214L relative to SEQ ID NO:1.

In some embodiments, the linalool synthase comprises the amino acid substitution V214I relative to SEQ ID NO:1.

In some embodiments, the linalool synthase comprises the amino acid substitution V214C relative to SEQ ID NO:1.

In some embodiments, the linalool synthase comprises the amino acid substitution V214N relative to SEQ ID NO:1.

In some embodiments, the linalool synthase comprises the amino acid substitution V214Q relative to SEQ ID NO:1.

In some embodiments, the linalool synthase comprises the amino acid substitution V214T relative to SEQ ID NO:1.

In some embodiments, the linalool synthase comprises the amino acid substitution V214A relative to SEQ ID NO:1.

In some embodiments, the linalool synthase comprises the amino acid substitution V214G relative to SEQ ID NO:1.

In some embodiments, the linalool synthase comprises the amino acid substitutions L72M and V214L, L72M and V214I, L72M and V214C, L72M and V214N, L72M and V214Q, L72M and V214T, L72M and V214A, L72M and V214G, L72C and V214L, L72C and V214I, L72C and V214C, L72C and V214N, L72C and V214Q, L72C and V214T, L72C and V214A, L72C and V214G, L72S and V214L, L72S and V214I, L72S and V214C, L72S and V214N, L72S and V214Q, L72S and V214T, L72S and V214A, L72S and V214G, L72T and V214L, L72T and V214I, L72T and V214C, L72T and V214N, L72T and V214Q, L72T and V214T, L72T and V214A, L72T and V214G, L72V and V214L, L72V and V214I, L72V and V214C, L72V and V214N, L72V and V214Q, L72V and V214T, L72V and V214A, L72V and V214G, L72A and V214L, L72A and V214I, L72A and V214C, L72A and V214N, L72A and V214Q, L72A and V214T, L72A and V214A, L72A and V214G, L72G and V214L, L72G and V214I, L72G and V214C, L72G and V214N, L72G and V214Q, L72G and V214T, L72G and V214A, or L72G and V214G relative to SEQ ID NO:1.

In some embodiments, the linalool synthase comprises the amino acid substitution L72M and V214L relative to SEQ ID NO:1.

In some embodiments, the linalool synthase comprises the amino acid substitution L72M and V214I relative to SEQ ID NO:1.

In some embodiments, the linalool synthase comprises, or consists, of an amino acid sequence having at least 70%, 75%, 80%, 85%, 90%, 95%, 99%, or 100% sequence identity to one or more of the amino acid sequences of SEQ ID NOs:2, 3, 4, 5, or 6.

The present invention also provides a nucleic acid encoding a linalool synthase as described herein, an expression vector comprising the nucleic acid, and a cell comprising said linalool synthase, nucleic acid or expression vector. The cell may be a microorganism, e.g. bacteria, gram-positive bacteria, gram-negative bacteria, *E. coli* or *Halomonas* spp.

The present invention also describes the use of a linalool synthase, a nucleic acid, an expression vector, or a cell for use in a method, optionally an in vitro or ex vivo method, for producing linalool.

The present invention also provides a method comprising catalysis of the conversion of geranyl pyrophosphate to linalool using a linalool synthase variant comprising one or more amino acid substitutions.

In some embodiments, the method which comprises catalysis of the conversion of geranyl pyrophosphate to linalool uses a linalool synthase mutant which comprises an amino acid sequence comprising a substitution corresponding to one or more of the L72 and V214 relative to SEQ ID NO:1.

In some embodiments, the method which comprises catalysis of the conversion of geranyl pyrophosphate to linalool uses a linalool synthase mutant which comprises one or more substitutions corresponding to the following amino acid substitutions relative to SEQ ID NO:1: L72M, V214L and V214I.

In some embodiments, the method which comprises catalysis of the conversion of geranyl pyrophosphate to linalool uses a linalool synthase mutant which comprises the amino acid substitution V214L relative to SEQ ID NO:1.

In some embodiments, the method which comprises catalysis of the conversion of geranyl pyrophosphate to linalool uses a linalool synthase mutant which comprises the amino acid substitution V214I relative to SEQ ID NO:1.

In some embodiments, the method which comprises catalysis of the conversion of geranyl pyrophosphate to linalool uses a linalool synthase mutant which comprises the amino acid substitutions L72M and V214L relative to SEQ ID NO:1.

In some embodiments, the method which comprises catalysis of the conversion of geranyl pyrophosphate to linalool uses a linalool synthase mutant which comprises the amino acid substitutions L72M and V214I relative to SEQ ID NO:1.

In some embodiments, the method of conversion of geranyl pyrophosphate to linalool results in a product in which the linalool:nerolidol ratio is greater than one of 2.20, 3, 5, 10, 20, or 30.

In some embodiments, the method of conversion of geranyl pyrophosphate to linalool results in a yield of nerolidol of less than one of 159 mg/$L_{org}^{-1}$, 100 mg/$L_{org}^{-1}$, 50 mg/$L_{org}^{-1}$, 25 mg/$L_{org}^{-1}$, 10 mg/$L_{org}^{-1}$, or 5 mg/$L_{org}^{-1}$.

In some embodiments, the method of conversion of geranyl pyrophosphate to linalool results in a linalool yield of one of at least 200 mg/$L_{org}^{-1}$, 300 mg/$L_{org}^{-1}$, 400 mg/$L_{org}^{-1}$, 500 mg/$L_{org}^{-1}$, 600 mg/$L_{org}^{-1}$, 700 mg/$L_{org}^{-1}$, 800 mg/$L_{org}^{-1}$, 900 mg/$L_{org}^{-1}$, or 1000 mg/$L_{org}^{-1}$.

In some embodiments, the method of conversion of geranyl pyrophosphate to linalool results in a linalool yield of one of at least 200 mg/$L_{org}^{-1}$, 300 mg/$L_{org}^{-1}$, 400 mg/$L_{org}^{-1}$, 500 mg/$L_{org}^{-1}$, 600 mg/$L_{org}^{-1}$, 700 mg/$L_{org}^{-1}$, 800 mg/$L_{org}^{-1}$, 900 mg/$L_{org}^{-1}$, or 1000 mg/$L_{org}^{-1}$, and a nerolidol yield of less than 159 mg/$L_{org}^{-1}$, 100 mg/$L_{org}^{-1}$, 50 mg/$L_{org}^{-1}$, 25 mg/$L_{org}^{-1}$, 10 mg/$L_{org}^{-1}$, or 5 mg/$L_{org}^{-1}$.

In some embodiments, the method of conversion of geranyl pyrophosphate to linalool results in a product which nerolidol represents less than one of 25%, 10%, 5%, or 2% of total terpenoids.

In some embodiments, the method of conversion of geranyl pyrophosphate to linalool results in a product which linalool represents more than one of 75%, 80%, 85%, 90%, or 95% of total terpenoids.

In further embodiments, linalool is an intermediate for the production of other products of interest.

In other embodiments, linalool or linalool derivatives are produced through fermentation. In other embodiments, linalool or linalool derivatives are produced through microbial fermentation. In further embodiments, linalool or linalool derivatives are produced through bacterial fermentation or fungal fermentation. In other embodiments, linalool or linalool derivatives are produced through fermentation of *E. coli* or *Halomonas* spp.

In other embodiments, linalool or linalool derivatives are produced through microbial fermentation, wherein the micro-organism comprises a linalool synthase, a nucleic acid encoding a linalool synthase, or an expression vector comprising a nucleic acid encoding a linalool synthase, as described herein. In some embodiments, linalool or linalool derivatives are produced from a waste product feedstock. In further embodiments, linalool or linalool derivatives are produced from feedstocks which include food waste, sewage or waste water.

In some embodiments, the cell is engineered to produce geranyl pyrophosphate (GPP). In some embodiments, the cell is also transformed to express a geranyl pyrophosphate (GPP) production platform. In further embodiments, the GPP production platform comprises an exogenous, hybrid mevalonate (MVA) pathway and a GPP synthase. In further embodiments, the hybrid MVA pathway comprises an Acetyl-CoA acetyltransferase (atoB), HMG-CoA synthase (HMGS), HMG-CoA reductase (HMGR), mevalonate kinase (MK), phosphomevalonate kinase (PMK), phosphomevalonate decarboxylase (PMD) and isopentenyl diphosphate isomerase (idi).

The invention includes the combination of the aspects and preferred features described except where such a combination is clearly impermissible or expressly avoided.

SUMMARY OF THE FIGURES

Embodiments and experiments illustrating the principles of the invention will now be discussed with reference to the accompanying figures in which:

FIG. 7. Summary of plasmids used in the examples. Descriptions of pMVA (Leferink et al. 2016), pGPPSmTC/S38 (Karuppiah et al. 2017) and specific primers used in the development of the current invention are provided.

FIG. 12. Summary product profiles obtained for VVT and bLinS variants. Product profiles and monoterpenoid titres (mg $L_{org}^{-1}$) were determined from two-phase cultures with a nonane overlay for each E. coli strain containing the MVA pathway and a bLinS variant. Averages of 2-6 biological replicates and the corresponding standard deviations are shown. ND=Not Detected.

Figure 1:
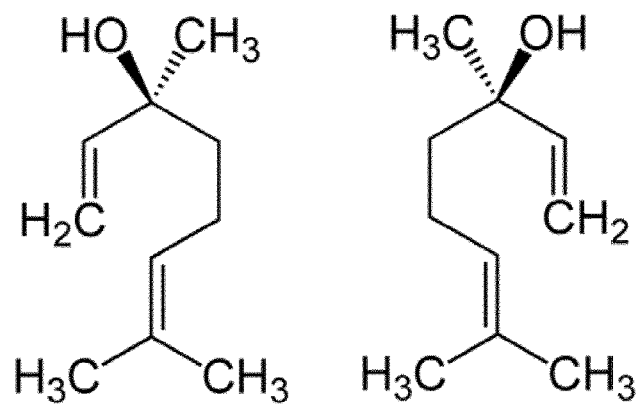
FIG. 1. Structure of linalool: (S)-(+)-linalool (left) and (R)-(−)-linalool (right)

Averages of 2-6 biological replicates and the corresponding standard deviations are shown. ND=Not Detected.

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

The present invention is based on the identification by the inventors of amino acid residues present in bLinS that could be modified so that the enzyme has a reduced preference for FPP and/or and increased preference for GPP. Through mutation of these previously unmodified amino acid residues, it was hypothesised that FPP may no longer fit in the active site, and therefore may not be converted to nerolidol, whilst maintaining the ability to convert GPP to linalool.

The inventors tested mutations at seven potential amino acid residues of interest, and surprisingly found that mutation of only two of these residues led to beneficial phenotypes. Mutation of L72 led to improvements in linalool yield and an improved linalool/nerolidol ratio, and mutation of V214 led to an improved linalool/nerolidol ratio. Additionally, a L72M-V214I double mutation led to much higher linalool production, and a L72M-V214L double mutation led to a high linalool/nerolidol ratio.

Terpenoids

Terpenoids are the most abundant and largest class (>80000) of natural products. Most are commonly found in plants, and their biological roles range from interspecies communication to intracellular signalling and defense against predatory species (Tholl, 2015). Their use is wide ranging as pharmaceuticals, herbicides, flavorings, fragrances, and biofuels (George et al., 2015). Despite the commercial interest in terpenoids, efforts to produce these in high yields have been hampered by lack of availability of sufficiently robust and high-activity terpene synthase enzymes, although efforts to synthesize terpenoids by synthetic biology routes have gathered pace in recent years (Leferink et al., 2016; Peralta-Yahya et al., 2012; Jongedijk et al., 2016; Zebec et al., 2016; Wang et al., 2015; Formighieri et al., 2016).

Terpenoids are synthesized from the isoprene building blocks dimethylallyl pyrophosphate (DMAPP) and isopentenyl pyrophosphate (IPP). Combination of DMAPP and IPP generates pyrophosphate substrates of varying carbon lengths, which are then utilized by terpene synthases to produce either monoterpenes (C10), sesquiterpenes (C15), diterpenes (C20), and others. Geranyl pyrophosphate (GPP), the substrate used by monoterpene synthases is formed by coupling one molecule of DMAPP with IPP, while farnesyl pyrophosphate (FPP), the substrate for sesquiterpenes, is synthesized by coupling three individual isoprene precursors (Oldfield et al., 2012).

Monoterpenes

Monoterpenes are a class of terpenes that consist of two isoprene units and have the molecular formula $C_{10}H_{16}$. Monoterpenes may be linear (acyclic) or contain rings. Modified terpenes, such as those containing oxygen functionality or missing a methyl group, are called monoterpenoids. Monoterpenes and monoterpenoids are diverse. They have relevance to the pharmaceutical, cosmetic, agricultural, and food industries. (Eberhard Breitmaier, 2006).

Linalool

Linalool is a monoterpene which is mainly used as a fragrance material in 60-80% of perfumed hygiene products. It is widely used in cosmetic products like perfumes, lotions, soaps, and shampoos and also in noncosmetic products like detergents and cleaning agents. Furthermore, during the manufacturing process of Vitamin E, linalool is a vital intermediate. As an important ingredient in a wide range of commercial products, the worldwide use of linalool exceeds 1000 metric tonnes per annum (Lapczynski, et al., 2008).

Both R and S isomers of linalool are found in nature with R-(-)-linalool being the most widely distributed in plant and flower extracts. The structure of R and S isomers of linalool are shown in FIG. 1. To our knowledge, for industrial use as a fragrance, the isomeric mixture is used. In this specification, reference to linalool includes R-linalool, S-linalool, and mixtures (e.g. racemic mixture) of R-linalool and S-linalool.

Linalool, as other monoterpenoids, is produced from isopentenyl pyrophosphate via the universal isoprenoid intermediate geranyl pyrophosphate, through a class of enzymes named monoterpene synthases.

Linalool Synthases

Figure 2:
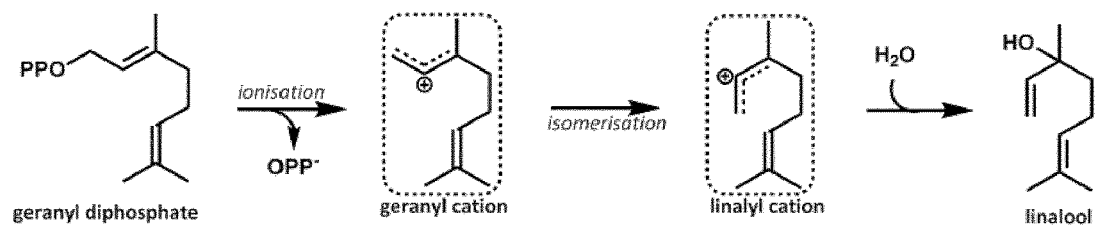
FIG. 2 Reaction catalysed by linalool synthase. The reaction is initiated by the metal-dependent ionisation of geranyl diphosphate resulting in the geranyl cation, which undergoes an isomerisation (via linalyl diphosphate) to the linalyl cation, which upon water attack yields linalool. Carbocation reaction intermediates are highlighted with dashed boxes.

The present invention provides methods using and compositions comprising linalool synthases. Linalool synthase as used herein generally refers to an enzyme capable of catalysing the conversion of geranyl diphosphate and water to linalool and diphosphate. Thus, the two substrates of this enzyme are geranyl diphosphate and $H_2O$, whereas its two products are linalool and diphosphate. The reaction is initiated by the metal-dependent ionisation of geranyl diphosphate resulting in the geranyl cation, which undergoes an isomerisation (via linalyl diphosphate) to the linalyl cation, which upon water attack yields linalool as shown in FIG. 2.

More specifically, S-linalool synthases convert geranyl diphosphate and water to (3S)-linalool and diphosphate, and R-linalool synthases convert geranyl diphosphate and water to (3R)-linalool and diphosphate. S-linalool synthases have the Enzyme Commission number 4.2.3.25, and R-linalool synthases have the Enzyme Commission number 4.2.3.26.

In aspects and embodiments of the present a linalool synthase may be an S- or R-linalool synthase.

Linalool synthases have been identified and characterised in a wide range of species, including plants *Arabidopsis thaliana* (UniProtKB—Q84UVO), *Oryza sativa* (UniProtKB—Q6ZH94), *Mentha aquatica* (UniProtKB—Q8H2B4), and *Ocimum basilicum* (UniProtKB—Q5SBP3), and bacteria *Streptomyces clavuligerus* (UniProtKB—D5SL78).

To date, available crystallographic structures for the monoterpene cyclases/synthases (mTC/S) that accept GPP as the substrate has been derived mainly for plant enzymes. Structures have been reported for bornyl diphosphate synthase (*Salvia officinalis*) (Whittington et al., 2002) limonene synthase (*Mentha spicata* and *Citrus sinensis*) (Hyatt et al., 2007; Kumar et al., 2017, Morehouse et al., 2017). 1,8-cineole synthase (*Salvia fruticosa*) (Kampranis et al., 2007) and γ-terpinene synthase (*Thymus vulgaris*) (Rudolph et al., 2016). Without exception, plant mTC/S contains two domains: a C-terminal α-helical catalytic domain that belongs to the class I terpenoid fold, and a N-terminal α-barrel domain with unclear function and that appears to be relictual. Though the overall sequence conservation is low, the structure of the α-helical fold is highly conserved. The active site has two conserved regions, the aspartate-rich motif (being one of the following sequences: DDXXD (SEQ ID NO:32), DDXXE (SEQ ID NO:33), DDXXXD (SEQ ID NO:34) or DDXXXE (SEQ ID NO:35)), and the NSE triad (being one of the following sequences: NDXXSXXRE (SEQ ID NO:36), NDXXSXXRD (SEQ ID NO:37), NDXXSXXKE (SEQ ID NO:38) or NDXXSXXKD (SEQ ID NO:39)), required for binding three catalytically essential $Mg^{2+}$ ions. Structures of bornyl diphosphate synthase and limonene synthases have been solved in complex with substrate analogues. In each case, GPP-analogues bind with their pyrophosphate moieties coordinated by the $Mg^{2+}$ ions and a network of residues that are proposed to assist with catalysis.

Recent reports have shown that terpene synthases are also widely distributed in bacteria, but the majority of these accept FPP as substrate and produce sesquiterpenes (Yamada et al., 2015; Yamada et al., 2015b) Ohnishi and co-workers characterized two bacterial mTC/S from *Streptomyces clavuligerus*, namely, 1,8-cineole synthase (Nakano et al., 2011) and linalool/nerolidol synthase, which can accept either GPP or FPP as substrate, leading to linalool or nerolidol products, respectively (Nakano et al., 2011b). Heterologous expression of these enzymes in *Streptomyces avermitilis* resulted in 1,8-cineole synthase (bCinS) producing 1,8-cineole and linalool/nerolidol synthase (bLinS) producing only linalool, indicating that bLinS is likely to function only as a mTC/S in this host (Yamada et al., 2015). The sequences of both bCinS and bLinS reveal they comprise ~330 amino acids in a single catalytic domain and lack the additional N-terminal α-barrel domain characteristic of plant enzymes. Surprisingly, no closely related homologues of both enzymes have been found in other bacteria (Dickschat, 2016). The bacterial mTC/S 2-methylisoborneol synthase is present in many bacteria. It accepts 2-methyl-GPP as substrate to produce 2-methylisoborneol. Unlike the bacterial mTC/S reported here, 2-methylisoborneol synthase has a considerably longer amino acid sequence (~400-500), and crystal structures have revealed a N-terminal proline-rich domain that is disordered along with a class I terpenoid cyclase fold C-terminal domain (Koksal et al., 2012).

It was recently shown by the inventors that *Streptomyces clavuligerus* bLinS and bCinS are active biocatalysts for monoterpene production using biocatalysis and metabolic engineering platforms (Karuppiah et al., 2017). In metabolically engineered monoterpene-producing *E. coli* strains, use of bLinS leads to 300-fold higher linalool production compared with the corresponding plant monoterpene synthase. With bCinS, 1,8-cineole is produced with 96% purity compared to 67% from plant species.

Structures of bLinS and bCinS (FIG. 3), and their complexes with fluorinated substrate analogues, show that these bacterial monoterpene synthases are similar to previously characterized sesquiterpene synthases which are also usually composed of only a single class I terpenoid cyclase fold domain (Gao et al., 2012). Molecular dynamics simulations suggest that these monoterpene synthases do not undergo large-scale conformational changes during the reaction cycle, making them attractive targets for structure-based protein engineering to expand the catalytic scope of these enzymes toward alternative monoterpene scaffolds. Comparison of the bLinS and bCinS structures indicates how their active sites steer reactive carbocation intermediates to the desired acyclic linalool (bLinS) or bicyclic 1,8-cineole (bCinS) products. The work reported here provides the analysis of structures for this important class of monoterpene synthase. This should now guide exploitation of the bacterial enzymes as gateway biocatalysts for the production of other monoterpenes and monoterpenoids (Karuppiah et al., 2017).

*Streptomyces clavuligerus* bLinS is a 330 amino acid polypeptide consisting of the sequence of SEQ ID NO:1 (UniProtKB—D5SL78).

In this specification "linalool synthase" refers to a linalool synthase from or derived from any species, in particular bacteria (e.g. *Streptomyces clavuligerus*) and plants (e.g. *Mentha aquatica*) and includes isoforms, fragments, variants or homologues of linalool synthase from any species. Homologues include orthologues.

As used herein, a "fragment", "variant" or "homologue" of a protein may optionally be characterised as having at least 50%, preferably one of 60%, 70%, 75%, 80%, 85%, 90%, 91%, 92%, 93%, 94%, 95%, 96%, 97%, 98%, 99% or 100% amino acid sequence identity to the amino acid sequence of the reference protein. Fragments, variants, isoforms and homologues of a reference protein may be characterised by the ability to perform a function performed by the reference protein.

A "fragment" generally refers to a fraction of the reference protein. A "variant" generally refers to a protein having an amino acid sequence comprising one or more amino acid substitutions, insertions, deletions or other modifications relative to the amino acid sequence of the reference protein, but retaining a considerable degree of sequence identity (e.g. at least 60%) to the amino acid sequence of the reference protein. An "isoform" generally refers to a variant of the reference protein expressed by the same species as the species of the reference protein. A "homologue" generally refers to a variant of the reference protein produced by a different species as compared to the species of the reference protein. For example, *Ocimum basilicum* linalool synthase (UniProtKB—Q5SBP3), and bacteria *Streptomyces clavuligerus* linalool synthase (UniProtKB—D5SL78) are homologues of one another. A "fragment" of a reference protein may be of any length (by number of amino acids), although may optionally be at least 25% of the length of the reference protein (that is, the protein from which the fragment is derived) and may have a maximum length of one of 50%, 75%, 80%, 85%, 90%, 91%, 92%, 93%, 94%, 95%, 96%, 97%, 98%, or 99% of the length of the reference protein.

A fragment of linalool synthase may have a minimum length of one of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, or 320 amino acids, and may have a maximum length of one of 15, 20, 25, 30, 40, 50, 100, 110, 120, 130, 140, 150, 160, 170, 180, 190, 200, 210, 220, 230, 240, 250, 260, 270, 280, 290, 300, 310, 320, or 330 amino acids.

Fragments, variants, isoforms and homologues of a linalool synthase may optionally be characterised by ability to catalyze conversion of geranyl diphosphate and water to linalool and diphosphate. Suitable conditions for analysis of this conversion are described throughout the specification and in Karuppiah et al. (2017).

In some embodiments the linalool synthase comprises a linalool synthase active site. As used herein, a "linalool synthase active site" refers to the region of a linalool synthase which contains the amino acids residues which contact the substrate and catalyse isomerisation of the substrate.

Linalool Synthase Variants

The present invention provides methods using and compositions comprising linalool synthase variants. The *Streptomyces clavuligerus* bLinS also accepts FPP and thus resulted in the formation of the sesquiterpene nerolidol as by-product (~30% of total product mixture) when produced in *E. coli* (Karuppiah et al., 2017). The generation of single, clean products is desirable, as this would require less downstream processing.

IspA, the gene encoding the native *E. coli* FPP synthase, is an essential gene in *E. coli*, therefore it cannot be knocked-out, and thus FPP cannot be removed from the bLinS substrate pool in *E. coli*. Alternatively, bLinS itself can be modified so that it reduced preference for FPP and/or an increased preference for GPP.

Inventors designed numerous linalool synthase variants based on the protein sequence of *Streptomyces clavuligerus* bLinS (SEQ ID NO:1). Several candidate amino acid residue positions were identified which could, upon mutation, reduce the substrate binding cleft and reduce enzyme preference for FPP and/or and increase preference for GPP.

Some, but not all, of these mutants had beneficial characteristics such as increased linalool yield, reduced nerolidol production and increased linalool:nerolidol ratios.

In some embodiments, the linalool synthase comprises an amino acid sequence comprising one or more of the following residues numbered relative to SEQ ID NO:1.

| Position | Residue |
|---|---|
| 72 | L, M, C, S, T, V, A, G |
| 214 | V, L, I, C, N, Q, T, A, G |

In some embodiments, the linalool synthase comprises an amino acid sequence having at least 70%, preferably one of 71%, 72%, 73%, 74%, 75%, 80%, 85%, 90%, 91%, 92%, 93%, 94%, 95%, 96%, 97%, 98%, 99% or 100% amino acid sequence identity to the amino acid sequence of SEQ ID NO:1, 2, 3, 4, 5, or 6.

In some embodiments, the linalool synthase comprises one or more amino acid substitutions relative to the amino acid sequence of the corresponding wild type linalool synthase (e.g. the linalool synthase having the amino acid sequence of SEQ ID NO:1). In some embodiments, the linalool synthase comprises a single mutation (i.e. only one amino acid substitution relative to the amino acid sequence of the corresponding wild type linalool synthase) or a double mutation (i.e. only two amino acid substitutions relative to the amino acid sequence of the corresponding wild type linalool synthase) and in other embodiments there are multiple mutations (i.e. more than two amino acid substitutions relative to the amino acid sequence of the corresponding wild type linalool synthase). In some embodiments, the corresponding wild type linalool synthase comprises the amino acid sequence of SEQ ID NO:1.

In other embodiments, the corresponding wild type linalool synthase is a linalool synthase that occurs naturally in any organism and can be, identified, isolated, sequenced and/or synthesized. This linalool synthase must have linalool synthase activity i.e. must be capable of catalysing the conversion of geranyl diphosphate and water to linalool and diphosphate.

In particular the present invention contemplates linalool synthases comprising amino acid substitutions corresponding to one or more of the following positions numbered relative to the amino acid sequence of SEQ ID NO:1: L72 and V214.

The skilled person is well able to identify corresponding positions to the indicated positions in linalool synthases other than linalool synthases from *Streptomyces clavuligerus* (SEQ ID NO:1). Corresponding positions can be identified e.g. by alignment of the amino acid sequence of a given linalool synthase to the amino acid sequence of SEQ ID NO:1. Sequence alignments for such purposes can be achieved in various ways known to a person of skill in the art, for instance, using publicly available computer software such as ClustalOmega (Soding, J. 2005, Bioinformatics 21, 951-960).

In some embodiments, the linalool synthase may comprise additional amino acids at the start or the end of the sequence i.e. the N-terminus or the C-terminus of the protein. In some cases, the additional amino acids are a leader sequence, a signal peptide, a transit peptide, a targeting signal, or a retention signal. Leader sequences (also known as a signal peptide or signal sequence) normally consist of a sequence of 5-30 hydrophobic amino acids, which form a single alpha helix. Secreted proteins and proteins expressed at the cell surface often comprise leader sequences. The leader sequence may be present in the newly-translated polypeptide (e.g. prior to processing to remove the leader sequence). Leader sequences, e.g. SEQ ID NO.13, are known for many proteins, and are recorded in databases such as GenBank, UniProt, Swiss-Prot, TrEMBL, Protein Information Resource, Protein Data Bank, Ensembl, and InterPro, and/or can be identified/predicted e.g. using amino acid sequence analysis tools such as SignalP (Petersen et al., 2011 Nature Methods 8: 785-786) or Signal-BLAST (Frank and Sippl, 2008 Bioinformatics 24: 2172-2176).

The *Streptomyces clavuligerus* (SEQ ID NO:1) linalool synthase may comprise additional amino acids at the start or end of the sequence. In some cases, the *Streptomyces clavuligerus* linalool synthase comprises 26 additional amino acids at the start of the sequence and has the amino acid sequence of SEQ ID NO:7. In some embodiments, the linalool synthase variants (e.g. SEQ ID NOs: 2-6) comprise amino acids at the start or end of the sequence. In some embodiments, the linalool synthase variants comprise 26 additional amino acids at the start of the sequence and have the amino acid sequences of SEQ ID NOs: 8-12.

In linalool synthase sequences which include a 26 amino acid leader sequence (e.g. SEQ ID NOs: 8-12), the substitution positions L72 and V214 according to SEQ ID NO:1 correspond to amino acids L98 and V240 respectively (SEQ ID NOs: 8-12). Corresponding residues can easily be determined through sequence alignment for polypeptides which comprise different length leader sequences.

In some embodiments, the leader sequence of the polypeptide of the present invention comprises, or consists of, an amino acid sequence having at least 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO:13.

It will similarly be appreciated that reference herein to a "corresponding" substitution refers to the same amino acid substitution at the corresponding position of the subject linalool synthase. In some embodiments, the substitutions are conservative substitutions, for example according to the following Table. In some embodiments, amino acids in the same block in the middle column are substituted. In some embodiments, amino acids in the same line in the rightmost column are substituted:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

In some embodiments, the substitution(s) may be functionally conservative. That is in some embodiments the substitution may not affect (or may not substantially affect) the activity of the linalool synthase. In some embodiments, the substitution(s) may yield an enzyme having similar linalool synthase activity and/or specific activity as compared to the linalool synthase activity/specific activity of the equivalent linalool synthase lacking the substitution(s).

In some embodiments, a linalool synthase comprising the substitution(s) give a yield of linalool which is ≥0.1 times and ≤2 times, ≥0.15 times and ≤1.75 times, ≥0.2 times and ≤1.5 times, ≥0.75 times and ≤1.25 times, e.g. ≥0.8 times and ≤1.2 times, ≥0.85 times and ≤1.15 times, ≥0.9 times and ≤1.1 times, ≥0.91 times and ≤1.09 times, ≥0.92 times and ≤1.08 times, ≥0.93 times and ≤1.07 times, ≥0.94 times and ≤1.06 times, ≥0.95 times and ≤1.05 times, ≥0.96 times and ≤1.04 times, ≥0.97 times and ≤1.03 times, ≤0.98 times and ≤1.02 times, or ≥0.99 times and ≤1.01 times the yield of linalool obtained using the equivalent linalool synthase lacking the substitution(s) in a comparable assay of linalool synthase activity.

In some embodiments, a linalool synthase comprising the substitution(s) give a yield of linalool which is more than 1 times, e.g. more than 1.1 times, 1.2 times, 1.3 times, 1.4 times, 1.5 times, 1.6 times, 1.7 times, 1.8 times, 1.9 times, 2.0 times, 2.1 times, 2.2 times, 2.3 times, 2.4 times, 2.5 times, 2.6 times, 2.7 times, 2.8 times, 2.9 times, 3.0 times, 3.5 times, 4.0 times, 5.0 times, 6.0 times, 7.0 times, 8.0 times, 9.0 times, or more than 10.0 times the yield of linalool obtained using the equivalent linalool synthase lacking the substitution(s) in a comparable assay of linalool synthase yield.

Figure 13:
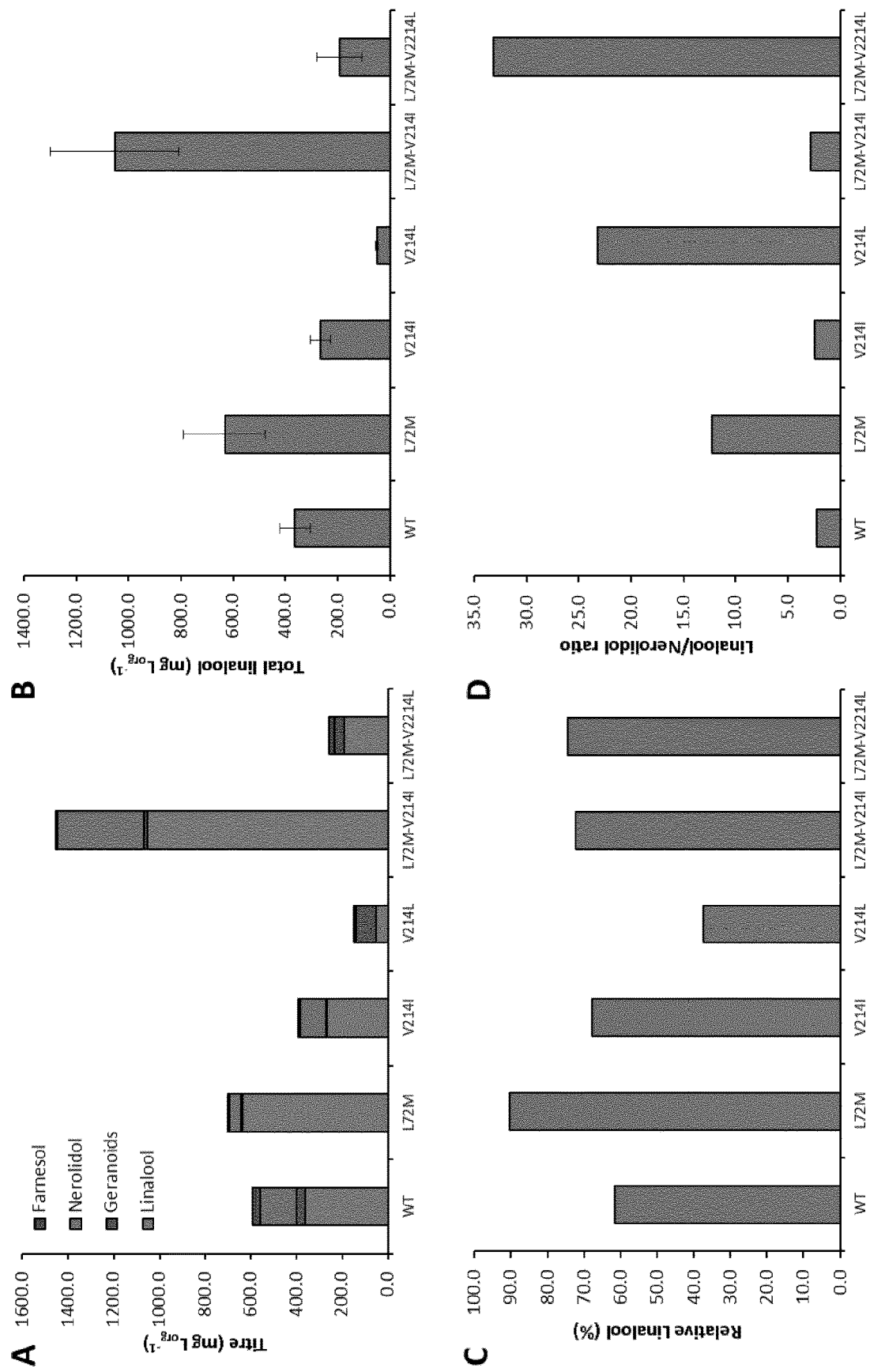
FIG. 13A-D. Comparison of product profiles obtained for L72-V214 double mutants compared to single mutants with favourable properties. A) Full product profiles: bars show farnesol (top), nerolidol (second from top), geranoids (third from top) and linalool (bottom), B) Linalool titres, C) Relative linalool content, and D) linalool/nerolidol ratios FIG. 14. Summary of product profiles obtained for WT and bLinS L72 and V214 variants. Product profiles and monoterpenoid titres (mg $L_{org}^{-1}$) were determined from two-phase cultures with a nonane overlay for each E. coli strain containing the MVA pathway and a bLinS variant.

By way of illustration, a linalool synthase comprising the amino acid sequence of SEQ ID NO:1 and comprising the amino acid substitutions L72M and V214I is demonstrated in the experimental examples of the present disclosure to produce a yield of linalool which is ~2.9 times greater than the yield of the equivalent linalool synthase lacking the substitutions—see FIGS. 13 and 14. Linalool yields can be determined through methods known in the art (e.g. Leferink et al. 2016 and Karuppiah et al., 2017), but as an example, the present disclosure determined linalool yields through GC-MS analysis of the recovered terpenoid product mixture. Compound identification was carried out using authentic standards and comparison to reference spectra in the NIST library of MS spectra and fragmentation patterns. Identified products were quantified in order to determine yields (e.g. linalool yield).

In some embodiments, a linalool synthase comprising the substitution(s) give a linalool:nerolidol ratio which is ≥0.1 times and ≤2 times, ≥0.15 times and ≤1.75 times, ≥0.2 times and ≤1.5 times, ≥0.75 times and ≤1.25 times, e.g. ≥0.8 times and ≤1.2 times, ≥0.85 times and ≤1.15 times, ≥0.9 times and ≤1.1 times, ≥0.91 times and ≤1.09 times, ≥0.92 times and ≤1.08 times, ≥0.93 times and ≤1.07 times, ≥0.94 times and ≤1.06 times, ≥0.95 times and ≤1.05 times, ≥0.96 times and ≤1.04 times, ≥0.97 times and ≤1.03 times, ≥0.98 times and ≤1.02 times, or ≥0.99 times and ≤1.01 times the linalool:nerolidol ratio obtained using the equivalent linalool synthase lacking the substitution(s) in a comparable assay of linalool synthase products.

In some embodiments, a linalool synthase comprising the substitution(s) give a linalool:nerolidol ratio which is more than 1 times, e.g. more than 1.1 times, 1.2 times, 1.3 times, 1.4 times, 1.5 times, 1.6 times, 1.7 times, 1.8 times, 1.9 times, 2.0 times, 2.1 times, 2.2 times, 2.3 times, 2.4 times, 2.5 times, 2.6 times, 2.7 times, 2.8 times, 2.9 times, 3.0 times, 3.5 times, 4.0 times, 5.0 times, 6.0 times, 7.0 times, 8.0 times, 9.0 times, 10.0 times, 11.0 times, 12.0 times, 13.0 times, 14.0 times, 15.0 times 16 times, 17 times, 18 times, 19 times, or more than 20.0 times the yield of linalool obtained using the equivalent linalool synthase lacking the substitution(s) in a comparable assay of linalool synthase products.

By way of illustration, a linalool synthase comprising the amino acid sequence of SEQ ID NO:1 and comprising the amino acid substitutions L72M and V214L is demonstrated in the experimental examples of the present disclosure to produce a linalool:nerolidol ratio which is ~15.1 times greater than the linalool:nerolidol ratio of the equivalent linalool synthase lacking the substitutions—see e.g. FIGS. 13 and 14. Linalool yields can be determined through methods known in the art (e.g. Leferink et al. 2016 and Karuppiah et al., 2017), but as an example, the present disclosure determined linalool yields through GC-MS analysis of the recovered terpenoid product mixture. Compound identification was carried out using authentic standards and comparison to reference spectra in the NIST library of MS spectra and fragmentation patterns. Identified products were quantified in order to determine yields (e.g. linalool yield).

In particular, linalool synthases comprising substitutions/combinations of substitutions corresponding to the following substitutions/combinations of substitutions are contemplated: L72M, V214I, and V214L.

In some embodiments, the linalool synthase comprises, or consists of, the amino acid sequence of SEQ ID NO:1, 2, 3, 4, or 5, or an amino acid sequence having at least 70%, preferably one of 80%, 85%, 90%, 91%, 92%, 93%, 94%, 95%, 96%, 97%, 98%, 99% or 100% amino acid sequence identity to the amino acid sequence of SEQ ID NO:1, 2, 3, 4, 5 or 6.

The linalool synthase of the present invention displays linalool synthase activity. Linalool synthases having activity can be determined by means known to the skilled person. For example, linalool synthase activity can be evaluated by analysis of the ability of the enzyme to catalyse conversion of geranyl diphosphate and water to linalool and diphosphate. Such assays can be performed e.g. as described in Example 2 herein. Products of reactions can be analysed e.g. by gas chromatography mass spectrometry (GC-MS) as described herein.

In some embodiments, the linalool synthase has increased activity as compared to activity of a reference protein, e.g. wild type bLinS (SEQ ID NO:1).

Increased Linalool synthase activity can be determined by the detection of an increased yield of linalool at the end of an assay for such activity as compared to the yield of linalool obtained using the reference protein in a comparable assay. In some embodiments a linalool synthase having increased activity gives a yield of linalool which is more than 1 times, e.g. more than 1.1 times, 1.2 times, 1.3 times, 1.4 times, 1.5 times, 1.6 times, 1.7 times, 1.8 times, 1.9 times, 2.0 times, 2.1 times, 2.2 times, 2.3 times, 2.4 times, 2.5 times, 2.6 times, 2.7 times, 2.8 times, 2.9 times, 3.0 times, 3.5 times, 4.0 times, 5.0 times, 6.0 times, 7.0 times, 8.0 times, 9.0 times, or more than 10.0 times the yield of linalool obtained using the reference protein in a comparable assay.

Linalool Yields

The present invention provides methods using and compositions comprising linalool synthase variants with the ability to produce higher yields of linalool compared with the corresponding wild type linalool synthase.

Linalool yields can be determined through methods known in the art. By way of example, methods used to determine subsequently presented values are as follows:

A pGPPSmTC/S plasmid harbouring native or variant bLinS genes is co-transformed with pMVA into *E. coli* DH5α and inoculated in terrific broth (TB) supplemented with 0.4% glucose in glass screw capped vials, and induced for 24-72 h at 30° C. with 50 μM (isopropyl β-D-1-thiogalactopyranoside) IPTG and 25 nM anhydro-tetracycline (aTet). A 20% n-nonane layer is added to capture the volatile terpenoids products. After induction, the nonane overlay is collected, dried over anhydrous $MgSO_4$ and mixed at a 1:1 ratio with ethyl acetate containing 0.01% (v/v) sec-butyl benzene as internal standard.

GC-MS analysis is then performed. The samples are injected onto an Agilent Technologies 7890B GC equipped with an Agilent Technologies 5977A MSD. The products are separated on a DB-WAX column (30 m'0.32 mm i.d., 0.25 μM film thickness, Agilent Technologies). The injector temperature is set at 240° C. with a split ratio of 20:1 (1 μl injection). The carrier gas is helium with a flow rate of 1 ml min-1 and a pressure of 5.1 psi. The following oven program is used: 50° C. (1 min hold), ramp to 68° C. at 5° C. min-1 (2 min hold), and ramp to 230° C. at 25° C. min-1 (2 min hold). The ion source temperature of the mass spectrometer (MS) is set to 230° C. and spectra were recorded from m/z 50 to m/z 250. Compound identification is carried out using authentic standards and comparison to reference spectra in the NIST library of MS spectra and fragmentation patterns. Linalool yields can be accurately determined from these spectra.

Wild type linalool synthase from *Streptomyces clavuligerus* (SEQ ID NO:1) is shown in the examples to produce a linalool yield of 363.3±57.9 mg $L_{org}^{-1}$. The present invention provides linalool synthase variants which produce a linalool yield greater than 363.3±57.9 mg $L_{org}^{-1}$.

In some embodiments, the present invention provides linalool synthase variants which produce a linalool yield greater than 400 mg $L_{org}^{-1}$. For example, linalool mutant bLinS-L72M produces a yield of 429.1±12.1 mg $L_{org}^{-1}$.

In further embodiments, the present invention provides linalool synthase variants which produce a linalool yield greater than 1000 mg $L_{org}^{-1}$. For example, linalool mutant bLinS-L72M-V214I produces a yield of 1054.0±245.2 mg $L_{org}^{-1}$.

Accordingly, in some embodiments, the present invention provides linalool synthase variants which produce a linalool yield greater than one of 363, 400, 450, 500, 550, 600, 650, 700, 750, 800, 850, 900, 950, 1000, or 1050 mg $L_{org}^{-1}$.

Linalool yield improvements are vital to increase the productivity of linalool biosynthesis. Previous studies have shown that linalool yields are higher when bacterial linalool synthases are expressed in bacteria compared with the expression of plant linalool synthases in bacteria. This is the first time that it has been demonstrated that even greater improvements in yield can be achieved through the mutation of bacterial linalool synthases.

Linalool:nerolidol Ratios

Bacterial linalool synthase catalyses the conversion of geranyl pyrophosphate to linalool. Linalool is the desired product for industry. However, bacterial linalool synthase also accepts FPP as a substrate and produces the sesquiterpene nerolidol as by-product (~30% of total product mixture) when produced in *E. coli* (Karuppiah et al., 2017).

In addition to increased yields, the generation of clean products is desirable, as this would require less downstream processing. To do this, the linalool:nerolidol ratio needs to be increased in the products of linalool synthase.

Linalool and nerolidol yields can be determined through methods known in the art in order to determine linalool:nerolidol ratios. By way of example, methods used to determine subsequently presented values are as follows:

A pGPPSmTC/S plasmid harbouring native or variant bLinS genes is co-transformed with pMVA into *E. coli* DH5a and inoculated in terrific broth (TB) supplemented with 0.4% glucose in glass screw capped vials, and induced for 24-72 h at 30° C. with 50 μM (isopropyl β-D-1-thiogalactopyranoside) IPTG and 25 nM anhydro-tetracycline (aTet). A 20% n-nonane layer is added to capture the volatile terpenoid products.

After induction, the nonane overlay is collected, dried over anhydrous $MgSO_4$ and mixed at a 1:1 ratio with ethyl acetate containing 0.01% (v/v) sec-butyl benzene as internal standard.

The terpenoid product mixture is captured in the 20% n-nonane layer. Once collected, dried over anhydrous $MgSO_4$ and mixed at a 1:1 ratio with ethyl acetate containing 0.01% (v/v) sec-butyl benzene as internal standard, the sample can be used to determine the linalool:nerolidol ratio in the terpenoid product mixture.

GC-MS analysis is then performed. The samples are injected onto an Agilent Technologies 7890B GC equipped with an Agilent Technologies 5977A MSD. The products were separated on a DB-WAX column (30 m×0.32 mm i.d., 0.25 μM film thickness, Agilent Technologies). The injector temperature is set at 240° C. with a split ratio of 20:1 (1 μl injection). The carrier gas is helium with a flow rate of 1 ml $min^{-1}$ and a pressure of 5.1 psi. The following oven program is used: 50° C. (1 min hold), ramp to 68° C. at 5° C. $min^{-1}$ (2 min hold), and ramp to 230° C. at 25° C. $min^{-1}$ (2 min hold). The ion source temperature of the mass spectrometer (MS) is set to 230° C. and spectra were recorded from m/z 50 to m/z 250. Compound identification is carried out using authentic standards and comparison to reference spectra in the NIST library of MS spectra and fragmentation patterns. Linalool and nerolidol yields can be accurately determined from these spectra. Linalool:nerolidol ratios are determined through simple calculations based on relative yields of each product.

Wild type linalool synthase from *Streptomyces clavuligerus* is shown in the examples to produce products with a linalool:nerolidol ratio of 2.28. The present invention provides linalool synthase variants which produce a product with a linalool:nerolidol ratio which is greater than 2.28.

In some embodiments, the present invention provides linalool synthase variants which produce products with a linalool:nerolidol ratio of greater than 9. For example, linalool mutant bLinS-L72M produces products with a linalool:nerolidol ratio of 9.80.

In further embodiments, the present invention provides linalool synthase variants which produce products with a linalool:nerolidol ratio of greater than 20. For example, linalool mutant bLinS-V214L produces products with a linalool:nerolidol ratio of 23.43.

In some embodiments, the present invention provides linalool synthase variants which produce products with a linalool:nerolidol ratio of greater than 30. For example, linalool mutant bLinS-L72M-V214L produces products with a linalool:nerolidol ratio of 33.20.

In some embodiments, the method of conversion of geranyl pyrophosphate to linalool results in a product in which the linalool:nerolidol ratio is greater than one of 2.20, 3, 5, 10, 15, 20, 25 or 30.

Product Terpenoid Composition

Figure 9:
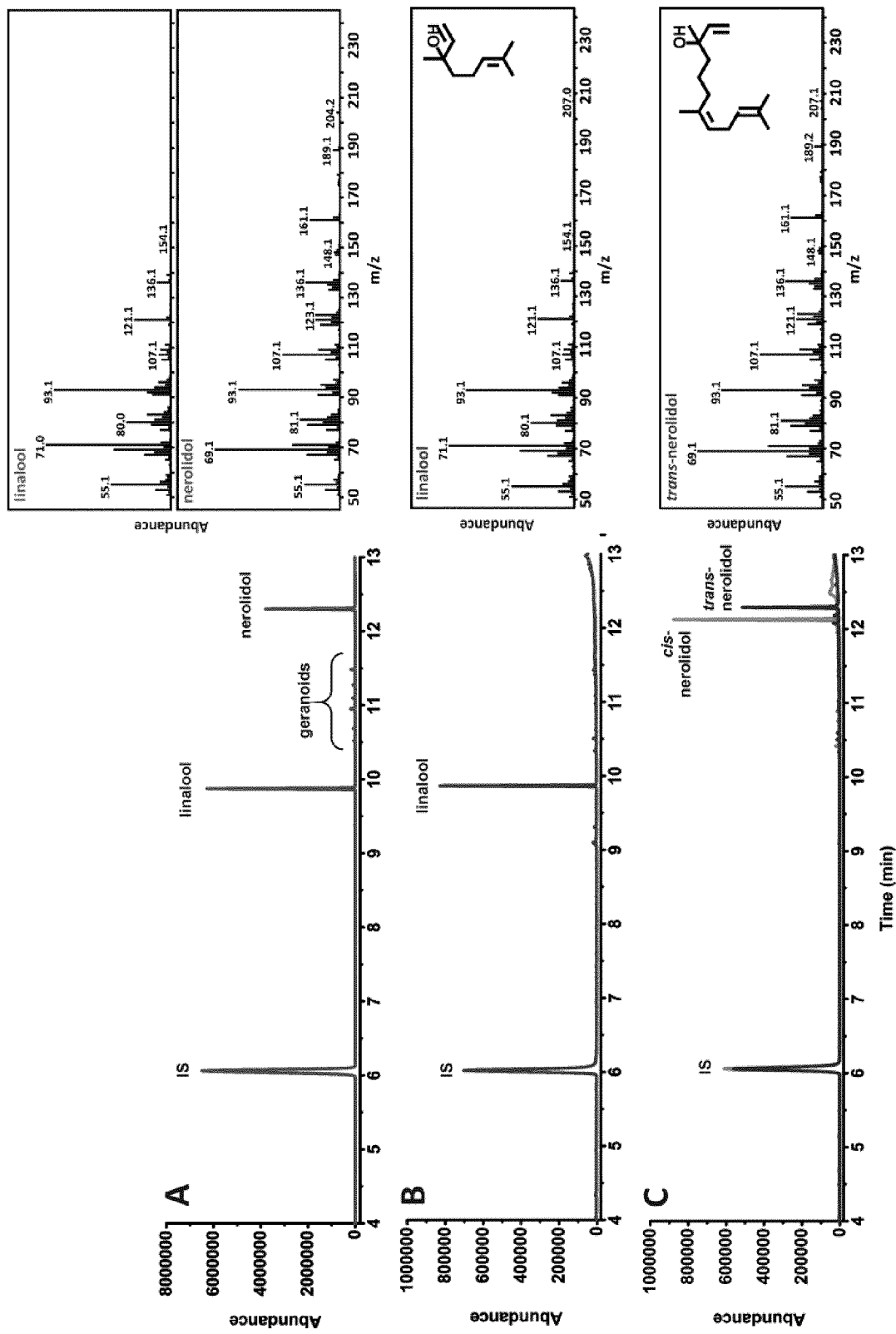
FIG. 9A-C. GC-MS analysis of the native bLinS product profile when inserted in an engineered E. coli strain capable of overproducing GPP. A) bLinS platform product profile. B) R-linalool standard (0.1 mg/ml). C) cis- and trans-nerolidol standards (0.1 mg ml-1). IS=internal standard (sec-butyl benzene).

The product profile of native bLinS expressed in an engineered *E. coli* strain capable of producing GPP was determined previously (Karuppiah et al. 2017) by GC-MS analysis of the organic overlay (FIG. 9). The obtained linalool titre was 360 mg $L_{org}^{-1}$, which constitutes approximately 65% of all terpenoids collected in the organic layer, nerolidol was 29% of the total and geraniol and derivatives, produced as a result of endogenous *E. coli* activity together constituted about 6% of the total terpenoid production.

To improve productivity of linalool production in industry, it would be beneficial to increase the percentage composition of linalool and decrease the percentage composition of nerolidol.

In some embodiments, the present invention provides linalool synthase variants which produce products wherein nerolidol represents less than 10% of total terpenoids within the product. For example, variant L72M has a lower level of nerolidol production (8% of total terpenoids production).

In some embodiments, the present invention provides linalool synthase variants which produce products wherein nerolidol represents less than 2% of total terpenoids within the product. For example, variant V214L has a lower level of nerolidol production (<2% of total terpenoids production).

In some embodiments, the method of conversion of geranyl pyrophosphate to linalool results in a product which nerolidol represents less than 25%, 10%, 5%, or 2% of total terpenoids.

In further embodiments, the present invention provides linalool synthase variants which produce products wherein linalool represents more than 65% of total terpenoids within the product. For example, in variant V214I, linalool represents 67.7% of total terpenoids within the product.

In further embodiments, the present invention provides linalool synthase variants which produce products wherein linalool represents more than 70% of total terpenoids within the product. For example, in variant L72M-V214L, linalool represents 74.1% of total terpenoids within the product.

In further embodiments, the present invention provides linalool synthase variants which produce products wherein linalool represents more than 65% of total terpenoids within the product. For example, in variant L72M, linalool represents 90.2% of total terpenoids within the product In some embodiments, the method of conversion of geranyl pyrophosphate to linalool results in a product which linalool represents more than one of 75%, 80%, 85%, 90%, or 95% of total terpenoids.

Linalool Derivatives

Linalool is involved in multiple enzymatic reactions, and as a result, numerous linalool derivatives can be generated e.g. 8-hydroxylinalool, geraniol and myrcene. These linalool derivatives can be used in the production of further derivatives. Therefore, linalool is not always the end product of a reaction, and can be used as an intermediate for the production of other products of interest.

For example, the action of the enzyme linalool 8-monooxygenase (EC:1.14.14.84) can enzymatically convert linalool to 8-hydroxylinalool through oxidoreductase activity. The action of the enzyme geraniol isomerase (EC 5.4.4.4) can catalyse the isomerization of (3S)-linalool to geraniol. In absence of oxygen the bifunctional linalool dehydratase-isomerase (EC 4.2.1.127) can catalyze the dehydration of linalool to myrcene.

Figure 4:
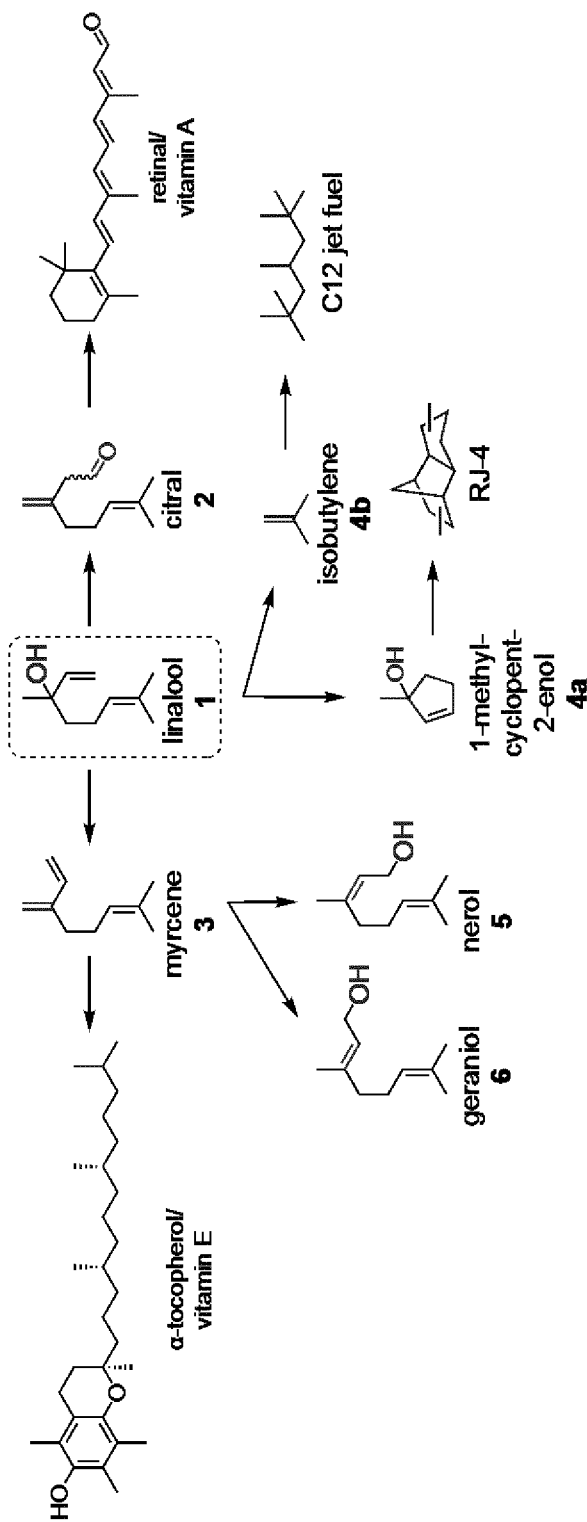
FIG. 4. Linalool (1) is a precursor to vitamin A via citral (2), to vitamin E via myrcene (3) and renewable fuels via the cyclic enol (4a) and isobutylene (4b). Nerol (5), geraniol (6) and citral (2) are also produced from linalool.

Linalool can be an intermediate for at least the following linalool derivatives: α-tocophrol/vitamin E, myrcene, geraniol, nerol, 1-methyl-cyclopent-2-enol, RJ-4, isobutylene, C12 jet fuel, citral, retinal/vitamin A (FIG. 4).

Methods of Linalool Production

Linalool and linalool derivatives can be produced through in vitro methods which utilise linalool synthases provided by this invention.

In one embodiment, linalool and linalool derivatives are produced through an in vitro method of fermentation. In some embodiments, linalool and linalool derivatives are produced through in vitro methods of bacterial fermentation. These methods may utilise *Escherichia coli* or *Halomonas* spp in the fermentation process.

In these methods of fermentation, micro-organisms such as bacteria and fungi grow on or in carbon rich media and produce linalool and/or linalool derivatives as metabolites. The microorganisms comprise a linalool synthase, a nucleic acid encoding a linalool synthase, or an expression vector comprising nucleic acid encoding a linalool synthase. This could be performed in sterile conditions in a fermentation tank or bioreactor as is typical for *E. coli*, or could be performed in non-sterile conditions with extremophile organisms such as *Halomonas* spp. The process may utilise batch methods, fed-batch methods, or continuous fermentation methods.

The medium may be any solid or liquid substance that provides carbon and nutrients to cells of interest to enable growth and linalool biosynthesis. In some embodiments, the carbon media may be nutrient broth, lysogeny broth (LB), terrific broth (TB), or any commonly used laboratory medium.

In other embodiments, the medium may be a waste product. A waste product is typically material discarded as useless in another process, material that has expired, material that has a low financial value, or feces, urine, and other material excreted in the life process. Waste products are a feedstock for such methods. Examples of waste product feedstock include wastewater, food waste and sewage. In preferred embodiments, the feedstock includes food waste.

GPP Production Platform

Some organisms that can be utilised in the production of linalool and linalool derivatives do not naturally produce geranyl pyrophosphate (GPP), which is the substrate of the linalool synthases described in this invention. In such organisms, the host is engineered to produce GPP. In some embodiments, the host is transformed to express a GPP production platform.

Figure 5:
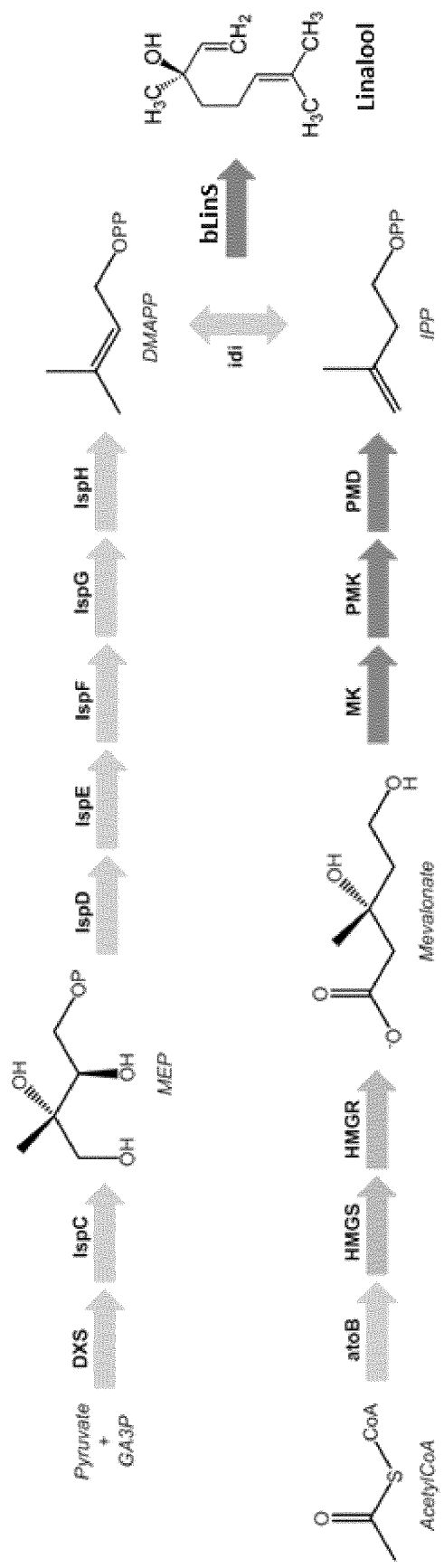
FIG. 5. Isoprenoid formation in the engineered E. coli strain. Top: endogenous MEP pathway. Bottom: exogenous hybrid MVA pathway. DXS=1-Deoxy-D-xylulose 5-phosphate synthase; IspC=1-Deoxy-D-xylulose 5-phosphate reductoisomerase; IspD=2-C-methyl-D-erythritol 4-phosphate cytidylyl transferase; IspE=4-diphosphocytidyl-2-C-methyl-D-erythritol kinase; IspF=2-C-methyl-D-erythritol 2,4-cyclodiphosphate synthase; IspG=(E)-4-Hydroxy-3-methyl-but-2-enyl pyrophosphate synthase; IspH=(E)-4-Hydroxy-3-methyl-but-2-enyl pyrophosphate reductase; atoB=Acetoacetyl-CoA thiolase; HMGS=3-hydroxy-3-methylglutaryl-CoA synthase; HMGR=3-hydroxy-3-methylglutaryl-CoA reductase; MK=mevalonate-5-kinase; PMK=phosphomevalonate kinase; PMD=mevalonate-5-pyrophosphate decarboxylase; idi=isopentenyl pyrophosphate isomerase; GPPS=geranyl diphosphate synthase FIG. 6. Oligonucleotides used for site-directed mutagenesis. Changed codons are underlined and changed nucleotides are in lower case. Forward oligonucleotides shown only.

Terpenoids are naturally synthesized from the universal C5 isoprenoid precursors isopentenyl diphosphate (IPP) and dimethylallyl diphosphate (DMAPP), the products of either the methylerythritol 4-phosphate (MEP) pathway, or the mevalonate-dependent (MVA) pathway The GPP production platform comprises an exogenous, hybrid mevalonate (MVA) pathway and a GPP synthase. The hybrid MVA pathway (pMVA) comprises an Acetyl-CoA acetyltransferase (atoB), HMG-CoA synthase (HMGS), HMG-CoA reductase (HMGR), mevalonate kinase (MK), phosphomevalonate kinase (PMK), phosphomevalonate decarboxylase (PMD) and isopentenyl diphosphate isomerase (id i). The combination of the MVA pathway and GPP synthase enable the generation of GPP from acetyl-CoA, which is readily available in most hosts. In some embodiments, the GPP production platform is as described by Leferink et al. (2016). In some embodiments, the GPP production platform is as described in FIG. 5.

Nucleic Acids, Expression Vectors, Cells and Compositions

The present invention also provides a nucleic acid, or a plurality of nucleic acids, encoding a linalool synthase.

In some embodiments the nucleic acid is DNA. In some embodiments the nucleic acid is RNA. The nucleic acid may be single-stranded or double-stranded. The nucleic acid may be provided in isolated/purified form, or within a host cell.

In general, short polynucleotides can be produced by synthetic means, involving a stepwise manufacture of the desired nucleic acid sequence one nucleotide at a time. Techniques for accomplishing this using automated techniques are readily available in the art. Longer polynucleotides will generally be produced using recombinant means, for example using PCR (polymerase chain reaction) cloning techniques. In some embodiments this will involve making a pair of primers (e.g. of about 15-30 nucleotides) to a region of the gene which it is desired to clone, bringing the primers into contact with DNA, performing a polymerase chain reaction under conditions which bring about amplification of the desired region, isolating the amplified fragment (e.g. by purifying the reaction mixture on an agarose gel) and recovering the amplified DNA.

The primers may be designed to contain suitable restriction enzyme recognition sites so that the amplified DNA can be cloned into a suitable cloning vector. Although in general the techniques mentioned herein are well known in the art, reference may be made in particular to Sambrook et al., 2001, Molecular Cloning: a laboratory manual, $3^{rd}$ edition, Cold Harbour Laboratory Press. Alternatively, InFusion cloning (described e.g. in Throop and LaBear, Curr Protoc Mol Biol. (2015) 110:3.20.1-3.20.23) or other cloning techniques may be used, such as Gibson Assembly (Gibson et al., Nat. Methods 2009; 6, 343-345), CRISPR/Cas9-based methods (Wang et al., (2015) BioTechniques 58:161-170), Sequence and Ligation Independent Cloning (SLIC; Nucleic Acids Res. 2012, 40: e55) and Modular Overlap-Directed Assembly with Linkers (MODAL; Nucleic Acids Res. (2014) 42.1: e7-e7).

The present invention further provides a vector, particularly an expression vector, comprising a nucleic acid or plurality of nucleic acids according to the present invention. The vector may be used to replicate the nucleic acid in a compatible host cell. Therefore, nucleic acids according to the present invention can be produced by introducing a polynucleotide into a replicable vector, introducing the vector into a compatible host cell and growing the host cell under conditions that bring about replication of the vector.

A "vector" as used herein is an oligonucleotide molecule (DNA or RNA) used as a vehicle to transfer foreign genetic material into a cell. The vector may be an expression vector for expression of the foreign genetic material in the cell. Such vectors may include a promoter and/or a ribosome binding site (RBS) sequence operably linked to the nucleotide sequence encoding the sequence to be expressed. A vector may also include a termination codon and expression enhancers. Such expression vectors are routinely constructed in the art of molecular biology and may for example involve the use of plasmid DNA and appropriate initiators, promoters, RBS, enhancers and other elements, such as for example polyadenylation signals, which may be necessary and which are positioned in the correct orientation in order to allow for protein expression.

Any suitable vectors, promoters, enhancers and termination codons known in the art may be used to express a polypeptide from a vector according to the invention. In some embodiments, the vector may be a plasmid, phage, MAC, virus, etc.

In some embodiments the vector may be a prokaryotic expression vector, e.g. a bacterial expression vector. In some embodiments the vector is a pGPPSmTC vector, e.g. as described in Karuppiah et al. 2017.

In some embodiments, the vector may be a eukaryotic expression vector. In some embodiments, the vector may be a eukaryotic expression vector, e.g. a vector comprising the elements necessary for expression of protein from the vector in a eukaryotic cell. In some embodiments, the vector may be a mammalian expression vector, e.g. comprising a cytomegalovirus (CMV) or SV40 promoter to drive protein expression.

Other suitable vectors would be apparent to persons skilled in the art. By way of further example in this regard we refer to Sambrook et al., 2001, Molecular Cloning: a laboratory manual, $3^{rd}$ edition, Cold Harbour Laboratory Press.

The term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. The resulting transcript may then be translated into a desired peptide or polypeptide. The promoter may be a T7 promoter.

In some embodiments, the vector may comprise element for facilitating translation of encoded protein from mRNA transcribed from the construct. For example, the construct may comprise a ribosomal binding site (RBS) such as a Shine-Dalgarno (SD) sequence upstream of the start codon.

In some embodiments, the vector may encode one or more response elements for modulating expression of the encoded protein(s). In some embodiments, the response element is an element that causes upregulation of gene or protein expression in response to treatment with a particular agent. For example, the agent may induce transcription of DNA encoding the protein(s) from a vector including a response element for the agent. In some embodiments the agent may be isopropyl β-D-1-thiogalactopyranoside (IPTG), and the vector may comprise a lac operator. Other induction agent/response element combinations are known in the art.

In some embodiments, the vector may encode one or more response elements for constitutive expression of the encoded protein(s), such that no induction is necessary.

In some embodiments the vector may comprise a transcription terminator sequence downstream of the sequences encoding to the protein or proteins of interest. In some embodiments the terminator may be a T7 terminator sequence. In some embodiments the vector may comprise a sequence encoding a detectable marker in-frame with the sequence encoding the protein of interest to facilitate detection of expression of the protein, and/or purification or isolation of the protein (e.g. a His, (e.g. 6×His), Myc, GST, MBP, FLAG, HA, E, or Biotin tag, optionally at the N- or C-terminus).

Also provided by the present invention is a cell comprising a linalool synthase, a nucleic acid or plurality of nucleic acids, or an expression vector according to the present invention.

The nucleic acids/expression vectors can be introduced into a cell by any suitable means, which are well known to the skilled person. In some embodiments the nucleic acids/expression vectors are introduced into a cell by transformation, transduction, conjugation, transfection or electroporation.

A cell comprising a linalool synthase according to the present invention may do so through expression from a nucleic acid/expression vector according to the present invention that has been introduced into the cell.

Cells and microorganisms contemplated for use with the present invention include prokaryotic and eukaryotic cells. For example, the prokaryotic cell may be a bacteria or archaea, and the eukaryotic microorganism may be a fungi, protist, or microscopic animal or microscopic plant organism. In some embodiments, the cells are isolated cells from a multicellular organism.

Microorganisms commonly used in commercial and industrial processes are contemplated, including microorganisms used for the commercial or industrial production of chemicals, enzymes or other biological molecules. In preferred aspects, the cells are of a bacterium. In some embodiments, the bacterium may be a Gram-positive bacterium. Gram-positive bacteria include bacteria from the genus *Bacillus*, bacteria from the genus *Listeria, Clostridium* (e.g. *C. difficile*), or coccus such as *Staphylococcus* (e.g. *S. aureus*), or *Streptococcus*. In some embodiments the bacterium may be a Gram-negative bacterium. Gram-negative bacteria may be defined as a class of bacteria that do not retain the crystal violet stain used in the Gram staining method of bacterial differentiation, making positive identification possible. Gram-negative bacteria include proteobacteria or bacteria of the family Enterobacteriaceae, such as *Escherichia coli, Salmonella* sp, *Shigella* sp, or bacteria selected from the genus *Pseudomonas, Helicobacter, Neisseria, Legionella, Halomonas, Klebsiella* or *Yersinia* bacterium.

In some embodiments, the fungi may blastocladiomycota, chytridiomycota, glomeromycota, microsporidia, or neocallimastigomycota. In some embodiments, the fungi may be dikarya (including deuteromycota), such as fungi of the ascomycota, including pezizomycotina, saccharomycotina, and taphrinomycotina; or basidiomycota, including agaricomycotina, pucciniomycotina, and ustilaginomycotina. In some embodiments, the fungi may be fungi of the entomophthoromycotina, kickxellomycotina, mucoromycotina, or zoopagomycotina.

In some embodiments, *Escherichia* bacteria such as *E. coli, Saccharomyces* yeast such as *S. cerevisiae* and cyanobacteria are contemplated for use in the present invention. In some embodiments the polypeptides may be prepared by cell-free-protein synthesis (CFPS), e.g. according using a system described in Zemella et al. Chembiochem (2015) 16(17): 2420-2431, which is hereby incorporated by reference in its entirety.

The present invention also provides a method for producing a composition according to the invention, comprising (i) culturing a cell according to the present invention under conditions suitable for expression of encoded protein(s). In some embodiments the method further comprises (ii) isolating said expressed protein(s). The invention also encompasses the compositions produced by such methods.

The present invention also provides compositions comprising the cells, nucleic acids, expression vectors, and enzymes/combinations of enzymes according to the present invention. The compositions find use e.g. in methods for monoterpenoid biosynthesis according to the present invention.

Any bacterium may be used, such as laboratory strains (such as *E. coli* or *Bacillus subtilis*), or field strains. Preferred bacteria will be those that are organotrophic, e.g. chemoheterotrophic bacteria, capable of using biomass or compounds derived therefrom as an energy source.

Preferred bacteria are robust bacteria, such as soil bacteria and/or extremophilic bacteria. Extremophilic bacteria include slight halophiles (able to grow in 1.7 to 4.8% NaCl), moderate halophiles (able to grow in 4.7 to 20% NaCl), extreme halophiles (able to grow in 20 to 30% NaCl), acidophiles (able to grow in conditions of low pH, such as below pH 5.0, e.g. pH 2 or below), alkaliphiles (able to grow in conditions of pH 8.5 or above), metallotolerant bacteria (able to survive in environments containing high concentrations of dissolved heavy metals), thermophiles (with an optimal growth temperature between about 41 and 122° C., e.g. strains of *Caldicellulosiruptor, Thermotoga, Thermoanaerobacterium, Pyrococcus*, and *Aeropyrum*), or polyextremophiles (bacterial possessing two or more extremophilic characteristics).

Especially preferred are halophilic bacteria. These are capable of growing in open non-sterile conditions. As these strains are salt tolerant, they will not be outcompeted so long as there is a high salt content.

Furthermore, the addition of a high salt buffer (e.g. at least a 3% salt solution) can be used to control competing bacteria. Halophilic bacteria include those of the genus *Halomonas*. Exemplary species of *Halomonas* have been described, including *H. alimentaria, H. alkaliantarctica, H. alkaliphila, H. almeriensis, H. andesensis, H. anticariensis, H. aquamarina, H. arcis, H. axialensis, H. beimenensis, H. bluephagenesis, H. boliviensis, H. campaniensis, H. campisalis, H. caseinilytica, H. cerina, H. cibimaris, H. cupida, H. daqiaonensis, H. daqingensis, H. denitrificans, H. desiderata, H. elongata, H. eurihalina, H. flava, H. fontilapidosi, H. garicola, H. gomseomensis, H. gudaonensis, H. halmophila, H. halocynthiae, H. halodenitrificans, halophila, H. hamiltonii, H. heilongjiangensis, H. huangheensis, H. hydrothermalis, H. ilicicola, H. janggokensis, H. jeotgali, H. johnsoniae, H. kenyensis, H. koreensis, H. korlensis, H. kribbensis, H. lutea, H. lutescence, H. magadiensis, H. maura, H. meridian, H. mongoliensis, H. muralis, H. nanhaiensis, H. neptunia, H. nitroreducens, H. olivaria, H. organivorans, H. pacifica, H. pantelleriensis, H. qiaohouensis, H. qijiaojingensis, H. ramblicola, H. rifensis, H. sabkhae, H. saccharevitans, H. salicampi, H. salifodinae, H. salina, H. sediminicola, H. shengliensis, H. sinaiensis, H. smyrnensis, H. songnenensis, H. stenophila, H. stevensii, H. subglaciescola, H. subterranean, H. suffidaeris, H. taeanensis, H. titanicae, H. urumqiensis, H. variabilis, H. ventosae,*

*H. venusta*, *H. vilamensis*, *H. xianhensis*, *H. xinjiangensis*, *H. zhangjiangensis*, and *H. zincidurans*.

Preferred *Halomonas* strains include *Halomonas* st. TQ10 and *Halomonas* st. TD01. Strain TQ10 is a genetically modified version of TD01 strain where the gene encoding MmP1 has been chromosomally integrated into the bacterium. The gene MmP1 is a T7-like promoter that enables the IPTG-inducible expression of recombinant proteins in *Halomonas* (Zhao H et al 2017 Novel T7-like expression systems used for *Halomonas*. Metabolic Engineering 39: p. 128-140 which is herein incorporated by reference in its entirety). Preferably, the *Halomonas* strain comprises the MmP1 gene, either chromosomally integrated or on a vector or plasmid.

In particular embodiments, *Escherichia* bacteria such as *E. coli*, *Saccharomyces* yeast such as *S. cerevisiae* and cyanobacteria are contemplated for use in the present invention.

In some embodiments the polypeptides may be prepared by cell-free-protein synthesis (CFPS), e.g. using a system described in Zemella et al. Chembiochem (2015) 16(17): 2420-2431, which is hereby incorporated by reference in its entirety.

Recombinant Production of Polypeptides

The polypeptides according to the present invention may be prepared according to methods for recombinant protein production known to the skilled person. Molecular biology techniques suitable for recombinant production are well known in the art, such as those set out in Green and Sambrook, Molecular Cloning: A Laboratory Manual (4th Edition), Cold Spring Harbor Press, 2012, which is hereby incorporated by reference in its entirety.

Expression may be from a nucleic acid sequence and/or an expression vector, e.g. a nucleic acid sequence or expression vector according to the present invention. Any suitable vectors, promoters, enhancers and termination codons known in the art may be used to express a peptide or polypeptide from an expression vector according to the invention. Expression may be from a cell according to the present invention. Any cell suitable for the expression of polypeptides may be used.

Production may involve culture or fermentation of cell modified to express the relevant polypeptide(s). The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted or expressed peptide or polypeptide. Culture, fermentation and separation techniques are well known to those of skill in the art, and are described, for example, in Green and Sambrook, Molecular Cloning: A Laboratory Manual (4th Edition; incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culturing the cells that express the polypeptide(s) of interest may be isolated. Any suitable method for separating proteins from cells known in the art may be used. In order to isolate the polypeptide it may be necessary to separate the cells from nutrient medium.

If the polypeptide(s) are secreted from the cells, the cells may be separated from the culture media that contains the secreted polypeptide(s) of interest by centrifugation.

If the polypeptide(s) of interest collect within the cell, protein isolation may comprise centrifugation to separate cells from cell culture medium, treatment of the cell pellet with a lysis buffer, and cell disruption e.g. by sonification, rapid freeze-thaw or osmotic lysis.

It may then be desirable to isolate the polypeptide(s) of interest from the supernatant or nutrient medium, which may contain other protein and non-protein components.

One approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins. Other methods for separating protein components include ion exchange chromatography and size chromatography. These may be used as an alternative to precipitation, or may be performed subsequently to precipitation.

Once the polypeptide(s) of interest have been isolated from the culture it may be desired or necessary to concentrate the peptide or polypeptide. A number of methods for concentrating proteins are known in the art, such as ultrafiltration and lyophilisation.

It will be appreciated that the polypeptides according to the present invention may be provided as components of larger polypeptides or polypeptide complexes. For example, the polypeptides described herein may be provided as fusion polypeptides. In some embodiments the polypeptides may comprise amino acid sequence(s) to facilitate expression, folding, trafficking, processing or purification, e.g. His, (e.g. 6×His), Myc GST, MBP, FLAG, HA, E, or Biotin tag, optionally at the N- or C-terminus.

Sequence Identity

Pairwise and multiple sequence alignment for the purpose of determining percent identity between two or more amino acid or nucleic acid sequences can be achieved in various ways known to a person of skill in the art, for instance, using publicly available computer software such as ClustalOmega (Söding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

Sequences

| SEQ ID NO: | DESCRIPTION | SEQUENCE |
|---|---|---|
| 1 | Linalool synthase from *Streptomyces clavuligerus* (L72 and V214 shaded) | MQEFEFAVPAPSRVSPDLARAR ARHLDWVHAMDLVRGEEARRRY EFSCVADIGAYGYPHATGADLD LCVDVLGWTFLFDDQFDAGDGR ERDALAVCAELTDLLWKGTAAT AASPPIVVAFSDCWERMRAGMS DAWRRRTVHEWVDYLAGWPTKL ADRAHGAVLDPAAHLRARHRTI CCRPLFALAERVGGYEVPRRAW HSSRLDGMRFTTSDAVIGMNEL HSFEKDRAQGHANLVLSLVHHG GLTGPEAVTRVCDLVQGSIESF LRLRSGLPELGRALGVEGAVLD RYADALSAFCRGYHDWGRGASR YTTRDHPGDLGLENLVARSSG |
| 2 | Linalool synthase variant bLinS-L72M | MQEFEFAVPAPSRVSPDLARAR ARHLDWVHAMDLVRGEEARRRY EFSCVADIGAYGYPHATGADLD LCVDVMGWTFLFDDQFDAGDGR ERDALAVCAELTDLLWKGTAAT AASPPIVVAFSDCWERMRAGMS DAWRRRTVHEWVDYLAGWPTKL ADRAHGAVLDPAAHLRARHRTI CCRPLFALAERVGGYEVPRRAW HSSRLDGMRFTTSDAVIGMNEL HSFEKDRAQGHANLVLSLVHHG GLTGPEAVTRVCDLVQGSIESF LRLRSGLPELGRALGVEGAVLD RYADALSAFCRGYHDWGRGASR YTTRDHPGDLGLENLVARSSG |
| 3 | Linalool synthase variant bLinS-V214L | MQEFEFAVPAPSRVSPDLARAR ARHLDWVHAMDLVRGEEARRRY EFSCVADIGAYGYPHATGADLD LCVDVLGWTFLFDDQFDAGDGR ERDALAVCAELTDLLWKGTAAT AASPPIVVAFSDCWERMRAGMS DAWRRRTVHEWVDYLAGWPTKL ADRAHGAVLDPAAHLRARHRTI CCRPLFALAERVGGYEVPRRAW HSSRLDGMRFTTSDALIGMNEL HSFEKDRAQGHANLVLSLVHHG GLTGPEAVTRVCDLVQGSIESF LRLRSGLPELGRALGVEGAVLD RYADALSAFCRGYHDWGRGASR YTTRDHPGDLGLENLVARSSG |
| 4 | Linalool synthase variant bLinS-V214I | MQEFEFAVPAPSRVSPDLARAR ARHLDWVHAMDLVRGEEARRRY EFSCVADIGAYGYPHATGADLD LCVDVLGWTFLFDDQFDAGDGR ERDALAVCAELTDLLWKGTAAT AASPPIVVAFSDCWERMRAGMS DAWRRRTVHEWVDYLAGWPTKL ADRAHGAVLDPAAHLRARHRTI CCRPLFALAERVGGYEVPRRAW HSSRLDGMRFTTSDAIIGMNEL HSFEKDRAQGHANLVLSLVHHG GLTGPEAVTRVCDLVQGSIESF LRLRSGLPELGRALGVEGAVLD RYADALSAFCRGYHDWGRGASR YTTRDHPGDLGLENLVARSSG |
| 5 | Linalool synthase variant bLinS-L72M-V214I | MQEFEFAVPAPSRVSPDLARAR ARHLDWVHAMDLVRGEEARRRY EFSCVADIGAYGYPHATGADLD LCVDVMGWTFLFDDQFDAGDGR ERDALAVCAELTDLLWKGTAAT AASPPIVVAFSDCWERMRAGMS DAWRRRTVHEWVDYLAGWPTKL ADRAHGAVLDPAAHLRARHRTI CCRPLFALAERVGGYEVPRRAW HSSRLDGMRFTTSDAIIGMNEL HSFEKDRAQGHANLVLSLVHHG GLTGPEAVTRVCDLVQGSIESF LRLRSGLPELGRALGVEGAVLD RYADALSAFCRGYHDWGRGASR YTTRDHPGDLGLENLVARSSG |
| 6 | Linalool synthase variant bLinS-L72M-V214L | MQEFEFAVPAPSRVSPDLARAR ARHLDWVHAMDLVRGEEARRRY EFSCVADIGAYGYPHATGADLD LCVDVMGWTFLFDDQFDAGDGR ERDALAVCAELTDLLWKGTAAT AASPPIVVAFSDCWERMRAGMS DAWRRRTVHEWVDYLAGWPTKL ADRAHGAVLDPAAHLRARHRTI CCRPLFALAERVGGYEVPRRAW HSSRLDGMRFTTSDALIGMNEL HSFEKDRAQGHANLVLSLVHHG GLTGPEAVTRVCDLVQGSIESF LRLRSGLPELGRALGVEGAVLD RYADALSAFCRGYHDWGRGASR YTTRDHPGDLGLENLVARSSG |
| 7 | Linalool synthase from *Streptomyces clevuligerus* with leader sequence | MKHHHHHHPMSDYDIPTTENLYF QGAMQEFEFAVPAPSRVSPDLAR ARARHLDWVHAMDLVRGEEARRR YEFSCVADIGAYGYPHATGADLD LCVDVLGWTFLFDDQFDAGDGRE RDALAVCAELTDLLWKGTAATAA SPPIVVAFSDCWERMRAGMSDAW RRRTVHEWVDYLAGWPTKLADRA HGAVLDPAAHLRARHRTICCRPL FALAERVGGYEVPRRAWHSSRLD GMRFTTSDAVIGMNELHSFEKDR AQGHANLVLSLVHHGGLIGPEAV TRVCDLVQGSIESFLRLRSGLPE LGRALGVEGAVLDRYADALSAFC RGYHDWGRGASRYTTRDHPGDLG LENLVARSSG |
| 8 | Linalool synthase variant bLinS-L72M with leader sequence | MKHHHHHHPMSDYDIPTTENLYF QGAMQEFEFAVPAPSRVSPDLAR ARARHLDWVHAMDLVRGEEARRR YEFSCVADIGAYGYPHATGADLD LCVDVMGWTFLFDDQFDAGDGRE RDALAVCAELTDLLWKGTAATAA GSPPIVVAFSDCWERMRAGMSDA WRRRTVHEVVVDYLAGWPTKLAD RAHAVLDPAAHLRARHRTICCRP LFALAERVGGYEVPRRAWHSSRL DGMRFTTSDAVIGMNELHSFEKD RAQGHANLVLSLVHHGGLTGPEA VTRVCDLVQGSIESFLRLRSGLP ELGRALGVEGAVLDRYADALSAF CRGYHDWGRGASRYTTRDHPGDL GLENLVARSSG |
| 9 | Linalool synthase variant bLinS-V214L with leader sequence | MKHHHHHHPMSDYDIPTTENLYF QGAMQEFEFAVPAPSRVSPDLAR ARARHLDWVHAMDLVRGEEARRR YEFSCVADIGAYGYPHATGADLD LCVDVLGWTFLFDDQFDAGDGRE RDALAVCAELTDLLWKGTAATAA SPPIVVAFSDCWERMRAGMSDAW RRRTVHEWVDYLAGWPTKLADRA HGAVLDPAAHLRARHRTICCRPL FALAERVGGYEVPRRAWHSSRLD GMRFTTSDALIGMNELHSFEKDR AQGHANLVLSLVHHGGLTGPEAV TRVCDLVQGSIESFLRLRSGLPE |

| SEQ ID NO: | DESCRIPTION | SEQUENCE |
|---|---|---|
| | | LGRALGVEGAVLDRYADALSAFC RGYHDWGRGASRYTTRDHPGDLG LENLVARSSG |
| 10 | Linalool synthase variant bLinS-V214I with leader sequence | MKHHHHHHPMSDYDIPTTENLYF QGAMQEFEFAVPAPSRVSPDLAR ARARHLDWVHAMDLVRGEEARRR YEFSCVADIGAYGYPHATGADLD LCVDVLGWTFLFDDQFDAGDGRE RDALAVCAELTDLLWKGTAATAA SPPIVVAFSDCWERMRAGMSDAW RRRTVHEWVDYLAGWPTKLADRA HGAVLDPAAHLRARHRTICCRPL FALAERVGGYEVPRRAVVHSSRL DGMRFTTSDAIIGMNELHSFEKD RAQGHANLVLSLVHHGGLTGPEA VTRVCDLVQGSIESFLRLRSGLP ELGRALGVEGAVLDRYADALSAF CRGYHDWGRGASRYTTRDHPGDL GLENLVARSSG |
| 11 | Linalool synthase variant bLinS-L72M-V214I with leader sequence | MKHHHHHHPMSDYDIPTTENLYF QGAMQEFEFAVPAPSRVSPDLAR ARARHLDWVHAMDLVRGEEARRR YEFSCVADIGAYGYPHATGADLD LCVDVMGWTFLFDDQFDAGDGRE RDALAVCAELTDLLWKGTAATAA SPPIVVAFSDCWERMRAGMSDAW RRRTVHEWVDYLAGWPTKLADRA HGAVLDPAAHLRARHRTICCRPL FALAERVGGYEVPRRAWHSSRLD GMRFTTSDAIIGMNELHSFEKDR AQGHANLVLSLVHHGGLTGPEAV TRVCDLVQGSIESFLRLRSGLPE LGRALGVEGAVLDRYADALSAFC RGYHDWGRGASRYTTRDHPGDLG LENLVARSSG |
| 12 | Linalool synthase variant bLinS-L72M-V214L with leader sequence | MKHHHHHHPMSDYDIPTTENLYF QGAMQEFEFAVPAPSRVSPDLAR ARARHLDWVHAMDLVRGEEARRR YEFSCVADIGAYGYPHATGADLD LCVDVMGWTFLFDDQFDAGDGRE RDALAVCAELTDLLWKGTAATAA SPPIVVAFSDCWERMRAGMSDAW RRRTVHEWVDYLAGWPTKLADRA HGAVLDPAAHLRARHRTICCRPL FALAERVGGYEVPRRAWHSSRLD GMRFTTSDALIGMNELHSFEKDR AQGHANLVLSLVHHGGLTGPEAV TRVCDLVQGSIESFLRLRSGLPE LGRALGVEGAVLDRYADALSAFC RGYHDWGRGASRYTTRDHPGDLG LENLVARSSG |
| 13 | Linalool synthase leader sequence | MKHHHHHHPMSDYDIPTTENLYF QGA |

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

EXAMPLES

In the following examples, the inventors demonstrate that certain mutations can improve the properties of bacterial linalool synthases. More specifically, they demonstrate that substitutions to linalool synthases can be used to both increase linalool yield and increase product linalool:nerolidol ratios.

Figure 3:
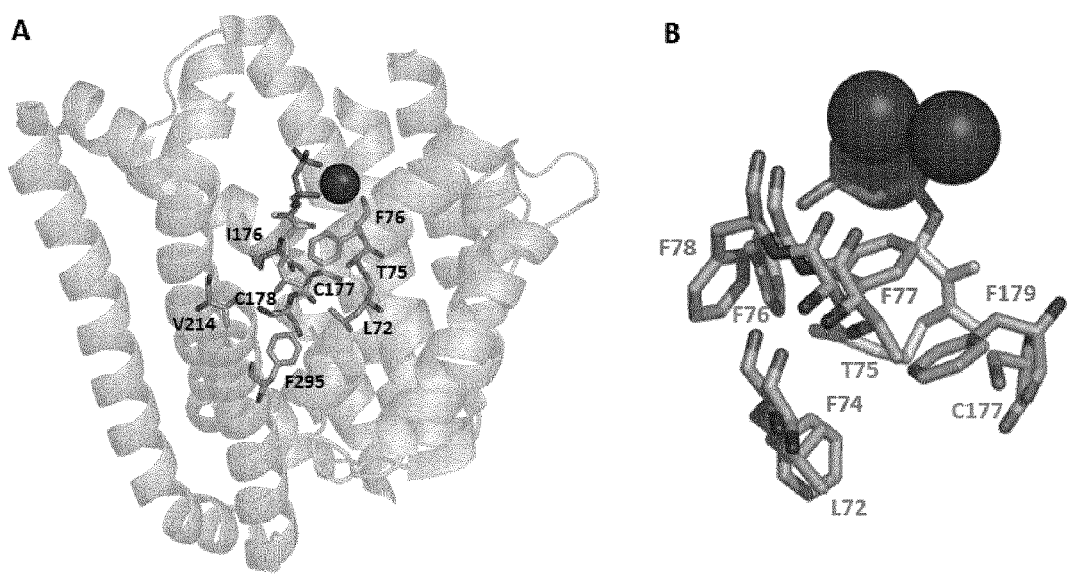
FIG. 3A-B. Identification of bLinS target residues from structural analysis of bLinS and bCinS. A) Cartoon representation of the bLinS structure in complex with FGPP (PDB: 5NX5). Residues identified for mutagenesis are indicated, the fluorinated GPP analogue (FGPP) is shown in light grey sticks and magnesium ions are represented as spheres. B) Active site overlay of bLinS and bCinS (PDB: 5NX7). The fluorinated substrate analogue (FGPP/FNPP) is shown in light grey sticks and magnesium ions are represented as spheres.

Example 1: Design of Engineered bLinS Variants with Limited Nerolidol Synthase Activity From the bLinS crystal structure (Karuppiah et al., 2017; FIG. 3), several candidate amino acid residue positions were identified which could, upon mutation, reduce the substrate binding cleft so the enzyme has a reduced preference for FPP and/or an increased preference for GPP.

Residues Leu72, Thr75 and Cys177 were chosen because the equivalent positions in the related bCinS enzyme contain the relatively large phenylalanine residue (FIG. 3B). bCinS has a smaller active site than bLinS and only accepts GPP as substrate. In addition, residues Leu72 and Thr75 are part of a previously identified plasticity region that is partly responsible for product outcome in plant mTC/S (Leferink et al., 2018). Residues Ile176, Cys178, Val214 and Phe295 were chosen because of their position at the bottom of the active site, and orientation towards the substrate analogue, which potentially allows for a reduction in the size of the active site cleft via the introduction of larger amino acids, thereby preventing the binding of FPP (FIG. 3A).

Example 2: Materials and Methods

Site-directed Mutagenesis

Mutations were introduced in bLinS using the QuikChange site-directed mutagenesis method (Stratagene) using plasmid pGPPSmTC/S38 encoding native bLinS (Karuppiah et al. 2017) as template. The oligonucleotides used are shown in FIG. 6. Correct insertion of mutations was confirmed by standard Sanger sequencing.

Linalool Production in E. coli

Figure 8:
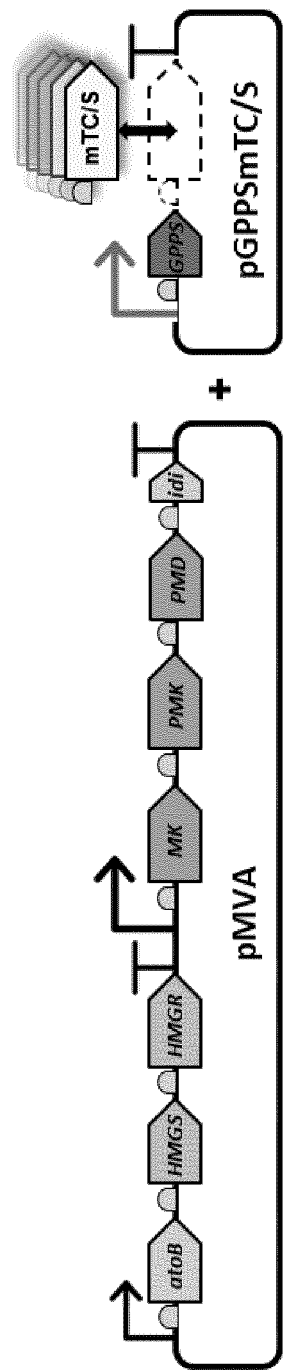
FIG. 8. Dual plasmid monoterpenoid production platform in E. coli. pMVA leads to IPP and DMAPP formation, plasmid pGPPSmTC/S leads to GPP and monoterpenoid formation. Variant mTC/S can be exchanged at position 2 to produce analogous production strains. In the case of the current invention, the mTC/S is a linalool synthase.

For monoterpenoid production a pGPPSmTC/S plasmid (FIG. 7) harbouring native or variant bLinS genes were co-transformed with pMVA into E. coli (FIG. 8) DH5α and grown as described previously (Leferink et al. 2016). Briefly, expression strains were inoculated in terrific broth (TB) supplemented with 0.4% glucose in glass screw capped vials, and induced for 48 h at 30° C. with 50 µM (isopropyl β-D-1-thiogalactopyranoside) IPTG and 25 nM anhydrotetracycline (aTet). A 20% n-nonane layer was added to capture the volatile terpenoid products. After induction, the nonane overlay was collected, dried over anhydrous MgSO$_4$ and mixed at a 1:1 ratio with ethyl acetate containing 0.01% (v/v) sec-butyl benzene as internal standard.

GC-MS Analysis

The samples were injected onto an Agilent Technologies 7890B GC equipped with an Agilent Technologies 5977A MSD. The products were separated on a DB-WAX column (30 m×0.32 mm i.d., 0.25 µM film thickness, Agilent Technologies). The injector temperature was set at 240° C. with a split ratio of 20:1 (1 µl injection). The carrier gas was helium with a flow rate of 1 ml min$^{-1}$ and a pressure of 5.1 psi. The following oven program was used: 50° C. (1 min hold), ramp to 68° C. at 5° C. min$^{-1}$ (2 min hold), and ramp to 230° C. at 25° C. min$^{-1}$ (2 min hold). The ion source temperature of the mass spectrometer (MS) was set to 230° C. and spectra were recorded from m/z 50 to m/z 250. Compound identification was carried out using authentic standards and comparison to reference spectra in the NIST library of MS spectra and fragmentation patterns as described previously (Leferink et al. 2016).

Example 3: bLinS Single Mutation Variants

The product profile of native bLinS expressed in an engineered E. coli strain capable of producing GPP was determined previously (Karuppiah et al. 2017) by GC-MS analysis of the organic overlay (FIG. 9). The obtained linalool titre was 360 mg $L_{org}^{-1}$, which constitutes approximately 65% of all terpenoids collected in the organic layer, nerolidol was 29% of the total and geraniol and derivatives, produced as a result of endogenous E. coli activity together constituted about 6% of the total terpenoid production.

Figure 10:
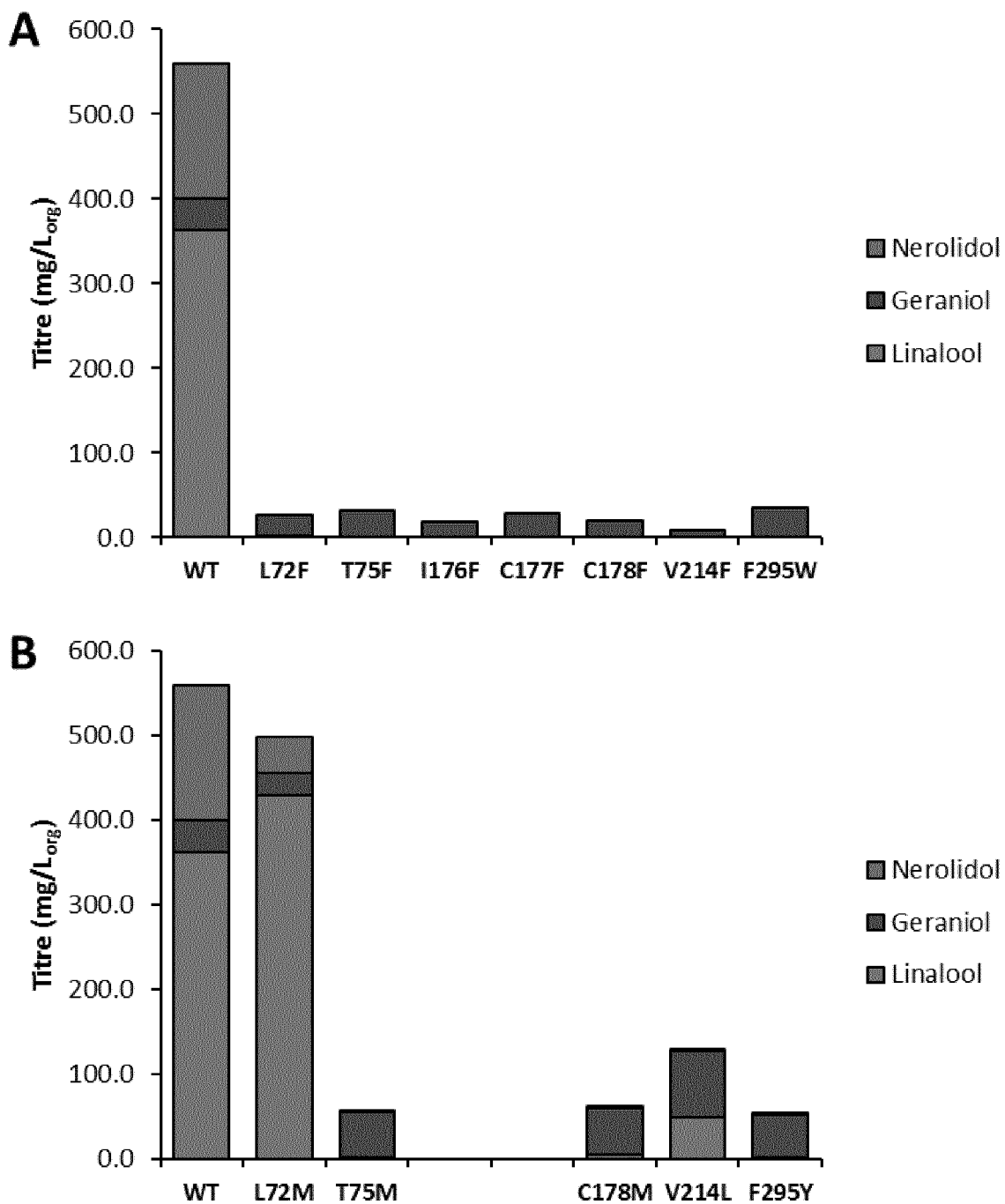
FIG. 10A-B. Comparison of product profiles wild-type bLinS (VVT) and variants. A) Variants generated in the first round of mutagenesis: the WT bar contains nerolidol (top section of bar), geraniol (middle section of bar), and linalool (bottom section of bar), variants generated in the first round of mutagenesis only produced geraniol. B) Variants generated in the second round of mutagenesis: WT and L72M bars contain nerolidol (top section of bar), geraniol (middle section of bar), and linalool (bottom section of bar), C178 and V214L produced geraniol (top section of bar), and linalool (bottom section of bar), and T75M and F295Y only produced geraniol.

In the first round of mutagenesis a bulky phenylalanine (Phe, F) residue was introduced at positions Leu72, Thr75, Ile176, Cys177, Cys178 and Val214, and a tryptophan (Trp, W) at position Phe295. In the related bCinS enzyme, the equivalent residues at positions 72, 75 and 177 are all Phe, and this enzyme has a smaller active site cavity and does not accept FPP as a substrate (Karuppiah et al. 2017). The product profiles obtained are shown in FIG. 10A. Only variant L72F still produces a very small amount of linalool (<3 mg $L_{org}^{-1}$) all other variants only produce geraniods at concentrations ranging from 10-35 mg $L_{org}^{-1}$.

Figure 11:
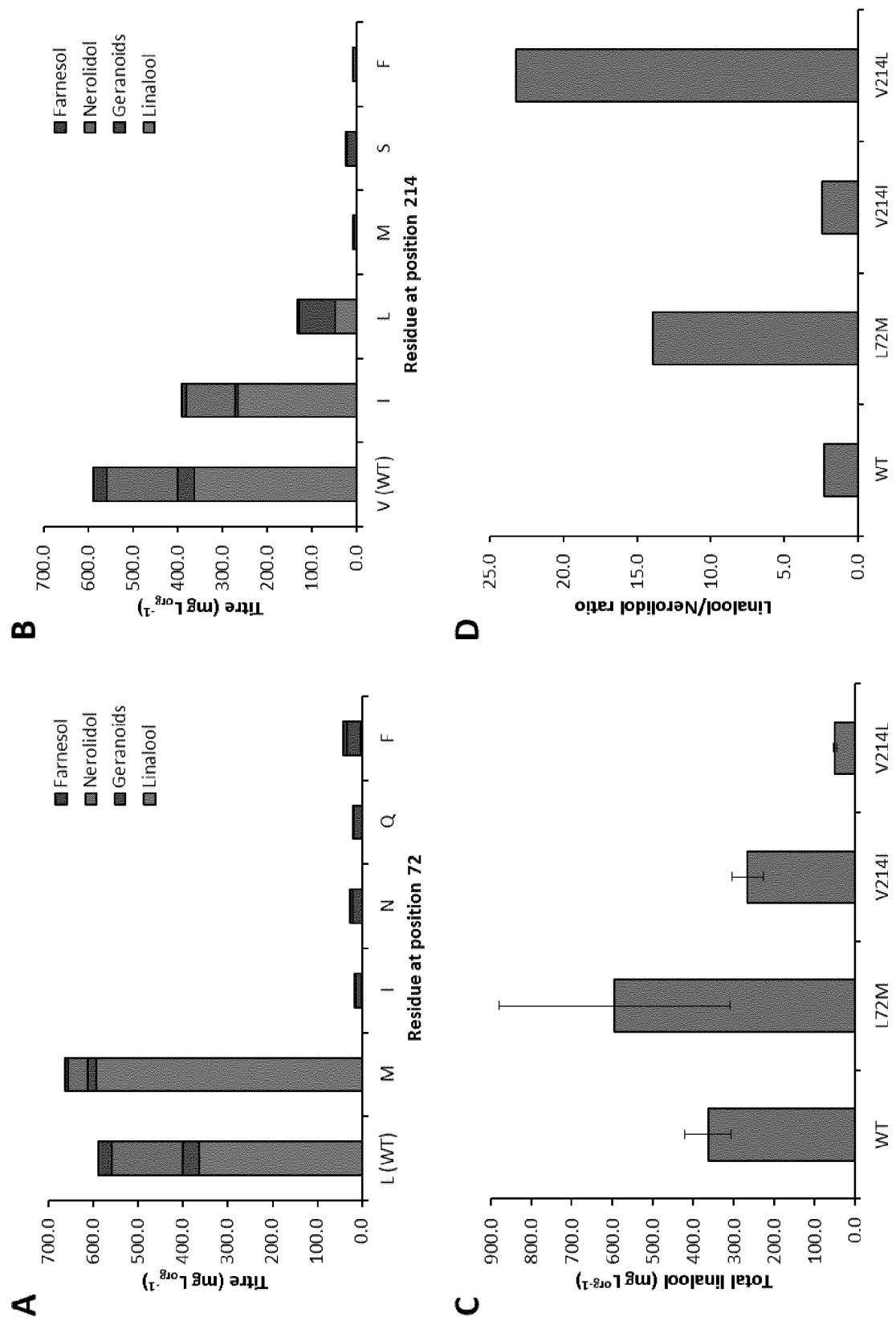
FIG. 11A-D. Comparison of product profiles obtained for (A) L72 variants: L(VVT) and M bars show farnesol (top), nerolidol (second from top), geranoids (third from top) and linalool (bottom), I, N, Q, and F bars mainly contain geranoids and low levels of other products. (B) V214 variants: V(VVT) and I bars show farnesol (top), nerolidol (second from top), geranoids (third from top) and linalool (bottom), the L bar shows low levels of nerolidol (top), geranoids (middle), and linalool (bottom), M, S, and F bars mainly contain geranoids and low levels of other products. The obtained linalool titres (C) and the linalool/nerolidol ratio (D) are shown for variants with improved properties.

A second round of mutagenesis was conducted on the same amino acid positions, this time with more subtle mutations, introducing amino acids that are only slightly bulkier than the original residues. A methionine (Met, M) was introduced at positions Leu72, Thr75 and C178, a leucine (Leu, L) was introduced at position Val214, and a tyrosine (Tyr, Y) was introduced at position Phe295. The product profiles obtained are shown in FIG. 10B. All second round variants were still capable of producing linalool, albeit ata very low level for variants T75M, C178M and F295Y (1-5 mg $L_{org}^{-1}$). However, these variants produce relatively large amounts of geraniol and derivatives (>50 mg $L_{org}^{-1}$), suggesting that the isomerisation step in the reaction cascade for the production of linalool is disrupted in these variants. Two variants showed favourable product profiles. Variant L72M has a linalool production slightly higher than WT bLinS (430 mg $L_{org}^{-1}$), and a lower nerolidol production (8% of total terpenoids production). Variant V214L, has a relatively low linalool titre compared to WT bLinS (50 mg $L_{org}^{-1}$), but the relative nerolidol production is even lower (<2%). Further amino acids have been introduced at positions 72 and 214 in a third round of mutagenesis, but only a limited number of variants show favourable linalool and/or a higher linalool/nerolidol ratio compared to native bLinS (FIG. 11), suggesting that the active site of this bacterial monoterpene synthase is less 'plastic' than similar enzymes from plants (Leferink et al., 2018). All titres are summarised in FIG. 12.

Example 4: bLinS Double Mutation Variants

Combinations of multiple mutations were also tested. A summary of these results compared to wild type and single mutants can be seen in FIGS. 13 and 14.

The L72M-V214I mutant has a similar product profile to the native wild type enzyme and the V214I single mutant, but it shows a much higher overall linalool yield (1054.0±245.2, ~2.9 times greater than wild type).

The L72M-V214L mutant has the highest linalool/nerolidol ratio (33.20, ~15.1 times greater than the linalool: nerolidol ratio of the wild type), but the overall production is lower than the wild type enzyme. In this L72M-V214L mutant, there is a slight increase in geraniol production (but not as much as the V214L single mutant).

REFERENCES

A number of publications are cited above in order to more fully describe and disclose the invention and the state of the art to which the invention pertains. Full citations for these references are provided below. The entirety of each of these references is incorporated herein.

1. Karuppiah, V.; Ranaghan K. E.; Leferink N. G. H.; Johannissen, L. O.; Shanmugam M.; Cheallaigh N. A.; Bennett, N. J.; Kearsey, L. J.; Takano, E.; Gardiner, J. M.; van der Kamp, M. W. Hay, S.; Mulholland, A. J.; Leys, D.; and Scrutton N. S. ACS Catal. 2017, 7, 6268-6282.
2. Tholl, D. Adv. Biochem. Eng./Biotechnol. 2015, 148, 63-106.
3. George, K. W.; Alonso-Gutierrez, J.; Keasling, J. D.; Lee, T. S. Adv. Biochem. Eng./Biotechnol. 2015, 148, 355-89.
4. Leferink, N. G. H.; Jervis, A. J.; Zebec, Z.; Toogood, H. S.; Hay, S.; Takano, E.; Scrutton, N. S. Chemistryselect 2016, 1, 1893-1896.
5. Peralta-Yahya, P. P.; Zhang, F.; del Cardayre, S. B.; Keasling, J. D. Nature 2012, 488, 320-8.
6. Jongedijk, E.; Cankar, K.; Buchhaupt, M.; Schrader, J.; Bouwmeester, H.; Beekwilder, J. Appl. Microbiol. Biotechnol. 2016, 100, 2927-38.
7. Zebec, Z.; Wilkes, J.; Jervis, A. J.; Scrutton, N. S.; Takano, E.; Breitling, R. Curr. Opin. Chem. Biol. 2016, 34, 37-43.
8. Wang, X.; Ort, D. R.; Yuan, J. S. Plant Biotechnol J. 2015, 13, 137-46.

9. Formighieri, C.; Melis, A. Photosynth. Res. 2016, 130, 123-135.
10. Oldfield, E.; Lin, F. Y. Angew. Chem., Int. Ed. 2012, 51, 1124-37.
11. Gao, Y.; Honzatko, R. B.; Peters, R. J. Nat. Prod. Rep. 2012, 29,
12. Eberhard Breitmaier. 2006. Terpenes: Flavors, Fragrances, Pharmaca, Pheromones. doi:10.1002/9783527609949.ch2.)
13. Lapczynski, A.; Letizia, C. S.; Api, A. M. Food Chem. Toxicol. 2008, 46, S190-2
14. Whittington, D. A.; Wise, M. L.; Urbansky, M.; Coates, R. M.; Croteau, R. B.; Christianson, D. W. Proc. Natl. Acad. Sci. U.S.A. 2002, 99, 15375-80.
15. Hyatt, D. C.; Youn, B.; Zhao, Y.; Santhamma, B.; Coates, R. M.; Croteau, R. B.; Kang, C. Proc. Natl. Acad. Sci. U.S.A. 2007, 104, 5360-5
16. Kumar, R. P.; Morehouse, B. R.; Matos, J. O.; Malik, K.; Lin, H.; Krauss, I. J.; Oprian, D. D. Biochemistry 2017, 56, 1716-1725.
17. Morehouse, B. R.; Kumar, R. P.; Matos, J. O.; Olsen, S. N.; Entova, S.; Oprian, D. D. Biochemistry 2017, 56, 1706-1715
18. Kampranis, S. C.; Ioannidis, D.; Purvis, A.; Mahrez, W.; Ninga, E.; Katerelos, N. A.; Anssour, S.; Dunwell, J. M.; Degenhardt, J.; Makris, A. M.; Goodenough, P. W.; Johnson, C. B. Plant Cell 2007, 19, 1994-2005.
19. Rudolph, K.; Parthier, C.; Egerer-Sieber, C.; Geiger, D.; Muller, Y. A.; Kreis, W.; Muller-Uri, F. Acta Crystallogr., Sect. F: Struct. Biol. Commun. 2016, 72, 16-23.
20. Yamada, Y.; Kuzuyama, T.; Komatsu, M.; Shin-Ya, K.; Omura, S.; Cane, D. E.; Ikeda, H. Proc. Natl. Acad. Sci. U.S.A. 2015, 112, 857-62.
21. Yamada, Y.; Arima, S.; Nagamitsu, T.; Johmoto, K.; Uekusa, H.; Eguchi, T.; Shin-ya, K.; Cane, D. E.; Ikeda, H. J. Antibiot. 2015, 68, 385-94.
22. Nakano, C.; Kim, H. K.; Ohnishi, Y. ChemBioChem 2011, 12, 1988-91.
23. Dickschat, J. S. Nat. Prod. Rep. 2016, 33, 87-110.
24. Koksal, M.; Chou, W. K.; Cane, D. E.; Christianson, D. W. Biochemistry 2012, 51, 3011-20.
25. Leferink, N. G. H.; Ranaghan, K. E.; Karuppiah, V.; Currin, A.; van der Kamp, M. W.; Mulholland, A. J.; Scrutton, N. S., ACS Catalysis 2018, 8, 3780-3791.

For standard molecular biology techniques, see Sambrook, J., Russel, D. W. *Molecular Cloning, A Laboratory Manual.* 3 ed. 2001, Cold Spring Harbor, New York: Cold Spring Harbor Laboratory Press

---

The invention claimed is:

1. A linalool synthase comprising an amino acid sequence having at least 90% sequence identity to the amino acid sequence of SEQ ID NO: 1, and an amino acid substitution corresponding to one or more of L72 and V214 relative to SEQ ID NO:1.

2. The linalool synthase according to claim 1, wherein the linalool synthase comprises one or more substitutions corresponding to the following amino acid substitutions relative to SEQ ID NO:1: L72M, V214L and V214I.

3. The linalool synthase according to claim 1, wherein the linalool synthase comprises the amino acid substitutions L72M and V214L relative to SEQ ID NO: 1.

4. The linalool synthase according to claim 1, wherein the linalool synthase comprises the amino acid substitutions L72M and V214I relative to SEQ ID NO: 1.

5. The linalool synthase according to claim 1, wherein the linalool synthase comprises an amino acid sequence having the sequence of SEQ ID NO:2, 3, 4, 5, 6, 7, 8, 9, 10, 11, or 12.

6. A nucleic acid encoding a linalool synthase according to claim 1.

7. An expression vector comprising the nucleic acid according to claim 6.

8. A cell comprising a linalool synthase according to claim 1.

9. An in vitro method comprising the conversion of geranyl pyrophosphate to linalool using a linalool synthase according to claim 1.

10. The method of claim 9, in which the linalool: nerolidol ratio in a produced terpenoid product mixture is greater than 2.20.

11. The method of claim 9, in which the linalool: nerolidol ratio in a produced terpenoid product mixture is greater than 9.00.

12. The method of claim 9, wherein the method results in a yield of nerolidol of less than 159 mg/$L_{org}^{-1}$.

13. The method of claim 9, wherein the method results in a linalool yield of at least 200 mg/$L_{org}^{-1}$.

14. The method of claim 9, wherein the yield of nerolidol is less than 159 mg/$L_{org}^{-1}$, and the yield of linalool is more than 400 mg/$L_{org}^{-1}$.

15. The method of claim 9, wherein nerolidol represents less than 25% of the total terpenoids in a produced terpenoid product mixture.

16. The method of claim 9, wherein linalool represents more than 75% of the total terpenoids in a produced terpenoid product mixture.

17. The method of claim 9, wherein linalool is an intermediate for the production of other products of interest.

18. The method of claim 9, wherein linalool or a linalool derivative is produced through a process of microbial fermentation.

19. A cell comprising a nucleic acid according to claim 6.

20. A cell comprising an expression vector according to claim 7.

21. The method of claim 9, wherein linalool or a linalool derivative is produced in *Halomonas* spp.

* * * * *